(12) United States Patent
Wunderlich et al.

(10) Patent No.: US 10,570,417 B2
(45) Date of Patent: Feb. 25, 2020

(54) RECOMBINANT ADENOVIRUS EXPRESSING TWO TRANSGENES WITH A BIDIRECTIONAL PROMOTER

(71) Applicant: Janssen Vaccines & Prevention B.V., Leiden (NL)

(72) Inventors: Kerstin Wunderlich, Kassel (DE); Jerôme H. H. V. Custers, Alphen aan den Rijn (NL); Jort Vellinga, Voorschoten (NL); Barbara Petronella Sanders, Amsterdam (NL)

(73) Assignee: Janssen Vaccines & Prevention B.V., Leiden (NL)

(*) Notice: Subject to any disclaimer, the term of this patent is extended or adjusted under 35 U.S.C. 154(b) by 99 days.

(21) Appl. No.: 15/566,073

(22) PCT Filed: Apr. 12, 2016

(86) PCT No.: PCT/EP2016/057982
§ 371 (c)(1),
(2) Date: Oct. 12, 2017

(87) PCT Pub. No.: WO2016/166088
PCT Pub. Date: Oct. 20, 2016

(65) Prior Publication Data
US 2018/0135075 A1    May 17, 2018

Related U.S. Application Data

(60) Provisional application No. 62/147,453, filed on Apr. 14, 2015.

(30) Foreign Application Priority Data

Apr. 14, 2015    (EP) .................................. 15163538

(51) Int. Cl.
*C12N 15/86* (2006.01)
*A61K 39/00* (2006.01)

(52) U.S. Cl.
CPC .............. *C12N 15/86* (2013.01); *A61K 39/00* (2013.01); *C12N 2710/10343* (2013.01); *C12N 2760/14134* (2013.01); *C12N 2760/14234* (2013.01); *C12N 2830/205* (2013.01); *C12N 2830/42* (2013.01); *C12N 2840/60* (2013.01)

(58) Field of Classification Search
None
See application file for complete search history.

(56) References Cited

U.S. PATENT DOCUMENTS

| | | |
|---|---|---|
| 5,057,540 A | 10/1991 | Kensil et al. |
| 5,122,458 A | 6/1992 | Post et al. |
| 5,559,099 A | 9/1996 | Wickham et al. |
| 5,837,511 A | 11/1998 | Falck-Pedersen et al. |
| 5,837,520 A | 11/1998 | Shabram et al. |
| 5,846,782 A | 12/1998 | Wickham et al. |
| 5,851,806 A | 12/1998 | Kovesdi et al. |
| 5,891,690 A | 4/1999 | Massie |
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,083,716 A | 7/2000 | Wilson et al. |
| 6,113,913 A | 9/2000 | Brough et al. |
| 6,225,289 B1 | 5/2001 | Kovesdi et al. |
| 6,261,823 B1 | 7/2001 | Tang et al. |
| 6,485,958 B2 | 11/2002 | Blanche et al. |
| 7,270,811 B2 | 9/2007 | Bout et al. |
| 7,326,555 B2 | 2/2008 | Konz, Jr. et al. |
| 8,932,607 B2 | 1/2015 | Custers et al. |
| 2008/0032300 A1* | 2/2008 | Chatellard ........... C12N 9/0069 435/6.16 |

FOREIGN PATENT DOCUMENTS

| | | |
|---|---|---|
| EP | 853660 A1 | 7/1998 |
| EP | 1230354 A2 | 8/2002 |
| EP | 1601776 A2 | 12/2005 |
| EP | 2128261 A1 | 12/2009 |
| WO | 9003184 A1 | 4/1990 |
| WO | 9014837 A1 | 12/1990 |
| WO | 9611711 A1 | 4/1996 |
| WO | 98/22588 A2 | 5/1998 |
| WO | 9839411 A1 | 9/1998 |
| WO | 99/12568 A1 | 3/1999 |
| WO | 99/41416 A2 | 8/1999 |
| WO | 1999/55132 A2 | 11/1999 |

(Continued)

OTHER PUBLICATIONS

Candolfi et al (Neuro-Oncology Jul. 2007, pp. 245-258). (Year: 2007).*
Addison et al (J Gen Virol Jul. 1997 vol. 78, No. 7: pp. 1653-1661). (Year: 1997).*
Int'l Search Report dated Jun. 20, 2016 in Int'l Application No. PCT/EP2016/057982.
Written Opinion dated Jun. 20, 2016 in Int'l Application No. PCT/EP2016/057982.
Chatellard et al, "The IE2 Promoter/Enhancer Region From Mouse CMV Provides High Levels of Therapeutic Protein Expression in Mammalian Cells," Biotechnology and Bioengineering, vol. 96, No. 1, pp. 106-117 (2007).
Abrahamsen et al, "Construction of an Adenovirus Type 7a E1A-Vector," Journal of Virology, vol. 71, No. 11, pp. 8916-8951 (1997).
Hsieh et al, "A Novel Targeting Modality to Enhance Adenoviral Replication by Vitamin D3 in Androgen-Independent Human Prostate Cancer Cells and Tumors," Cancer Research, vol. 62, pp. 3084-3092 (2002).

(Continued)

*Primary Examiner* — Catherine S Hibbert
(74) *Attorney, Agent, or Firm* — Panitch Schwarze Belisario & Nadel LLP

(57) ABSTRACT

The invention provides recombinant adenovirus (rAd) and rAd vectors comprising a bidirectional mouse CMV (mCMV) promoter operably linked to a first transgene in one direction and to a second transgene in the opposite direction. The invention also provides methods of making and using such rAd and rAd vectors.

11 Claims, 15 Drawing Sheets

Specification includes a Sequence Listing.

(56) References Cited

FOREIGN PATENT DOCUMENTS

| WO | 2000/29024 | A1 | 5/2000 |
|---|---|---|---|
| WO | 2000/32754 | A1 | 6/2000 |
| WO | 00/29024 | A9 | 11/2000 |
| WO | 2000/070071 | A1 | 11/2000 |
| WO | 01/02607 | A1 | 1/2001 |
| WO | 2001/66137 | A1 | 9/2001 |
| WO | 02/22080 | A2 | 3/2002 |
| WO | 2002/040665 | A2 | 5/2002 |
| WO | 2003/049763 | A1 | 6/2003 |
| WO | 03/061708 | A1 | 7/2003 |
| WO | 03/078592 | A2 | 9/2003 |
| WO | 2003/104467 | A1 | 12/2003 |
| WO | 2004/001032 | A2 | 12/2003 |
| WO | 2004004762 | A1 | 1/2004 |
| WO | 2004020971 | A2 | 3/2004 |
| WO | 2004037294 | A2 | 5/2004 |
| WO | 2004055187 | A1 | 7/2004 |
| WO | 2005002620 | A1 | 1/2005 |
| WO | 2005071093 | A2 | 8/2005 |
| WO | 2005080556 | A2 | 9/2005 |
| WO | 2006053871 | A2 | 5/2006 |
| WO | 2006108707 | A1 | 10/2006 |
| WO | 2006120034 | A1 | 11/2006 |
| WO | 2007073513 | A2 | 6/2007 |
| WO | 2007/104792 | A2 | 9/2007 |
| WO | 2007100908 | A2 | 9/2007 |
| WO | 2007/110409 | A1 | 10/2007 |
| WO | 2009026183 | A1 | 2/2009 |
| WO | 2009117134 | A2 | 9/2009 |
| WO | 2010/085984 | A1 | 8/2010 |
| WO | 2010/086189 | A2 | 8/2010 |
| WO | 2010096561 | A1 | 8/2010 |
| WO | 2011045378 | A1 | 4/2011 |
| WO | 2011045381 | A1 | 4/2011 |
| WO | 2013139911 | A1 | 9/2013 |
| WO | 2013139916 | A1 | 9/2013 |

OTHER PUBLICATIONS

Abbink et al, "Comparative Seroprevalance and Immunogenicity of Six Rare Serotype Recombinant Adenovirus Vaccine Vectors From Subgroups B and D," Journal of Virology, vol. 81, No. 9, pp. 4654-4663 (2007).

Amendola et al, "Coordinate Dual-Gene Transgenesis by Lentiviral Vectors Carrying Synthetic Bidirectional Promoters," Nature Biotechnology, vol. 23, No. 1, pp. 108-116 (2005).

Bangari and Mittal, "Development of Nonhuman Adenoviruses As Vaccine Vectors," Vaccine, vol. 24, No. 7, pp. 849-862 (2006).

Brough et al, "A Gene Transfer Vector-Cell Line System for Complete Functional Complementation of Adenovirus Early Regions E1 and E4," Journal of Virology, vol. 70, No. 9, pp. 6497-6501 (1996).

De Felipe et al, "Inhibition of 2A-Mediated 'Cleavage' of Certain Artificial Polyproteins Bearing N-Terminal Signal Sequences," Biotechnology Journal, vol. 5, pp. 213-223 (2010).

Belousova et al, "Circumventing Recombination Events Encountered With Production of a Clinical-Grade Adenoviral Vector With a Double-Expression Cassette," Molecular Pharmacology, vol. 70, No. 5, pp. 1488-1493 (2006).

Cohen et al, "Chimpanzee Adenovirus CV-68 Adapted as a Gene Delivery Vector Interacts With the Coxsackievirus and Adenovirus Receptor," Journal of General Virology, vol. 83, pp. 151-155 (2002).

Donnelly et al, "The 'Cleavage' Activities of Foot-And-Mouth Disease Virus 2A Site-Directed Mutants and Naturally Occurring '2A-Like' Sequences," Journal of General Virology, vol. 82, pp. 1027-1041 (2001).

Fallaux et al, "New Helper Cells and Matched Early Region 1-Deleted Adenovirus Vectors Prevent Generation of Replication Competent Adenoviruses," Human Gene Therapy, vol. 9, pp. 1909-1917 (1998).

Geisbert et al, "Recombinant Adenovirus Serotype 26 (Ad26) and Ad35 Vaccine Vectors Bypass Immunity to Ad5 and Protect Non-human Primates Against Ebolavirus Challenge," Journal of Virology, vol. 85, No. 9, pp. 4222-4233 (2011).

Havenga et al, "Novel Replication-Incompetent Adenoviral B-Group Vectors: High Vector Stability and Yield in PER. C6 Cells," Journal of General Virology, vol. 87, pp. 2135-2143 (2006).

Farina et al, "Replication-Defective Vector Based on a Chimpanzee Adenovirus," Journal of Virology, vol. 75, No. 23, pp. 11603-11613 (2001).

Goerke et al, "Development of a Novel Adenovirus Purification Process Utilizing Selective Precipitation of Cellular DNA," Biotechnology and Bioengineering, vol. 91, pp. 12-21 (2005).

Hoganson et al, "Development of a Stable Adenoviral Vector Formulation," Bioprocessing Journal, vol. 1, No. 1, pp. 43-48 (2002).

Gao et al, "A Cell Line for High-Yield Production of E1-Deleted Adenovirus Vectors Without the Emergence of Replication-Competent Virus," Human Gene Therapy, vol. 11, pp. 213-219 (2000).

Harro et al, "Safety and Immunogenicity of Adenovirus-Vectored Near-Consensus HIV Type 1 Clade B Gag Vaccines in Healthy Adults," AIDS Research and Human Retroviruses, vol. 25, No. 1, pp. 103-114 (2009).

Holman et al, "Two Complex, Adenovirus-Based Vaccines That Together Induce Immune Responses to All Four Denque Virus Serotypes," Clinical and Vaccine Immunology, vol. 14, No. 2, pp. 182-189 (2007).

Holterman et al, "Novel Replication-Incompetent Vector Derived From Adenovirus Type 11 (Ad11) for Vaccination and Gene Therapy: Low Seroprevalence and Non-Cross-Reactivity With Ad5," Journal of Virology, vol. 78, No. 23, pp. 13207-13215 (2004).

Lasaro et al, "New Insights on Adenovirus As Vaccine Vectors," Molecular Therapy, vol. 17, No. 8, pp. 1333-1339 (2009).

Hu et al, "Comparative Immunogenicity of Recombinant Adenovirus-Vectored Vaccines Expressing Different Forms of Hemagglutinin (HA) Proteins From the H5 Serotype of Influenza A Viruses in Mice," Virus Research, vol. 155, pp. 156-162 (2011).

Lemckert et al, "Generation of a Novel Replication-Incompetent Adenoviral Vector Derived From Human Adenovius Type 49: Manufacture on PER.C6 Cells, Tropism and Immunogenicity," Journal of General Virology, vol. 87, pp. 2891-2899 (2006).

Kobinger et al, "Chimpanzee Adenovirus Vaccine Protects Against Zaire Ebola Virus," Virology, vol. 346, Issue 2, pp. 394-401 (2006).

Mullick et al, "The Cumate Gene-Switch: A System for Regulated Expression in Mammalian Cells," BMC Biotechnology, vol. 6, No. 43, pp. DOI: 10.1186/1472-6750-6-43 (2006).

Nan et al, "Development of an Ad7 Cosmid System and Generation of an Ad7DE1DE3HIVMN Env/Rev Recombinant Virus," Gene Therapy, vol. 10, pp. 326-336 (2003).

Ophorst et al, "Immunogenicity and Protection of a Recombinant Human Adenovirus Serotype 35-Based Malaria Vaccine Against Plasmodium Yoelii in Mice," Infection and Immunity, vol. 74, No. 1, pp. 313-320 (2006).

Na et al, "Design of Ad5F35 Vectors for Coordinated Dual Gene Expression in Candidate Human Hematopoietic Stem Cells," Experimental Hematology, vol. 38, pp. 446-452 (2010).

Ogun et al, "The Oligomerization Domain of C4-Binding Protein (C4bp) Acts as an Adjuvant, and the Fusion Protein Comprised of the 19-Kilodalton Merozoite Surface Protein 1 Fused With the Murine C4bp Domain Protects Mice From Malaria," Infection and Immunity, vol. 76, No. 8, pp. 3817-3823 (2008).

Pham et al, "Concordant Activity of Transgene Expression Cassettes Inserted Into E1, E3, and E4 Cloning Sites in the Adenovirus Genome," J. Gene Med., vol. 11, No. 3, pp. 197 doi:10.1002/jgm. 1289 (2009).

Radosevic et al, "The Th1 Immune Response to Plasmodium Falciparum Circumsporozoite Protein is Boosted by Adenovirus Vectors 35 and 26 With a Homologous Insert," Clinical and Vaccine Immunology, vol. 17, No. 11, pp. 1687-1694 (2010).

Small et al, "Construction and Characterization of E1- and E3-Deleted Adenovirus Vectors Expressing Two Antigens From Two Separate Expression Cassettes," Human Gene Therapy, vol. 25, pp. 328-338 (2014).

(56) References Cited

OTHER PUBLICATIONS

Sullivan et al, "Accelerated Vaccination for Ebola Cirus Haemorrhagic Fever in Non-Human Primates," Nature, vol. 424, pp. 681-684 (2003).

Schepp-Berglind et al, "Complex Adenovirus-Mediated Expression of West Niles Virus C, PreM, E, and NS1 Proteins Induces Both Humoral and Cellular Immune Response," Clinical and Vaccine Immunology, vol. 14, No. 9, pp. 1117-1126 (2007).

Sullivan et al, "Immune Protection of Nonhuman Primates Against Ebola Virus With Single Low-Dose Adenovirus Vectors Encoding Modified GPs," PLoS Medicine, vol. 3, Issue 6, pp. 865-873 (2006).

Szymczak et al, "Correction of Multi-Gene Dificiency In Vivo Using a Single 'Self-Cleaving' 2A Peptide-Based Retroviral Vector," Nature Biotechnology, vol. 22, No. 5, pp. 589-594 (2004).

Tatsis et al, "A CD46-Binding Chimpanzee Adenovirus Vector as a Vaccine Carrier," Molecular Therapy, vol. 15, No. 3, pp. 608-617 (2007).

Vogels et al, "Replication-Deficient Human Adenovirus Type 35 Vectors for Gene Transfer and Vaccination: Efficient Human Cell Infection and Bypass of Preexisting Adenovirus Immunity," Journal of Virology, vol. 77, No. 15, pp. 8263-8271 (2003).

Zhou et al, "A Chimpanzee-Origin Adenovirus Vector Expressing the Rabies Virus Glycoprotein as an Oral Vaccine Against Inhalation Infection With Rabies Virus," Molecular Therapy, vol. 14, No. 5, pp. 662-672 (2006).

Vemula and Mittal, "Production of Adenovirus Vectors and Their Use As a Delivery System for Influenza Vaccines," Expert Opin. Biol. Ther., vol. 10, No. 10, pp. 1469-1487 (2010).

Vogels et al, "High-Level Expression From Two Independent Expression Cassettes in Replication-Incompetent Adenovirus Type 35 Vector," Journal of General Virology, vol. 88, pp. 2915-2924 (2007).

Zhou et al, "A Universal Influenza A Vaccine Based on Adenovirus Expressing Matrix-2 Ectodomain and Nucleoprotein Protects Mice From Lethal Challenge," Molecular Therapy, vol. 18, No. 12, pp. 2182-2189 (2010).

Ebert et al., "Tetracycline-Regulated Adenovirus Encoding Dominant-Negative Caspase-9 is Regulated in Rat Brain and Protects Against Neurotoxin-Induced Cell Death in Vitro, but Not in Vivo", Experimental Neurology, vol. 191, No. 1, pp. S80-S94 (Feb. 2005).

* cited by examiner

(A) Bivalent E1-E3 rHAdV design

ITR — ψ — ΔE1 — ΔE3 — E4 5orf6 — ITR hCMV ▸ gene 1 ▸ pA₁    hCMV ▸ gene 2 ▸ pA₂    Vogels et al., 2007 pA₂ ◂ gene 2 ◂ hCMV    inverted orientation

(B) Bivalent rHAd35.E1.EBOV-E3.SEBOV

E1 transgene region — 1 2 3 4 5 M P+ P- H₂O
E3 transgene region — 1 2 3 4 5 M P+ P- H₂O p5
p10
p15

Fig. 2

(A) rHAd35: Bivalent E1-F2A design

ITR — ψ — ΔE1 — ΔE3 — E4 5orf6 — ITR hCMV ▶ gene 1 — F2A — gene 2 — pA₁

(B)

eGFP-F2A-Luc

Luc-F2A-eGFP

MARV-F2A-SEBOV

Lanes: 1 2 3 4 5 P+ H₂O M

(C)

α-MARV

MARV-F2A-SEBOV | E1.MARV

α-SEBOV

MARV-F2A-SEBOV | E1.SEBOV

(A) rHAd35: Bivalent E1-E1 design

(B)

mCAG.Luc-hCMV.eGFP mCAG.MARV-hCMV.SEBOV

(C)

α-MARV mCAG.MARV-hCMV.SEBOV    E1.MARV

α-SEBOV mCAG.MARV-hCMV.SEBOV    E1.SEBOV

Fig. 4

Fig. 4 – continued (A) Bidirectional expression cassette (B)

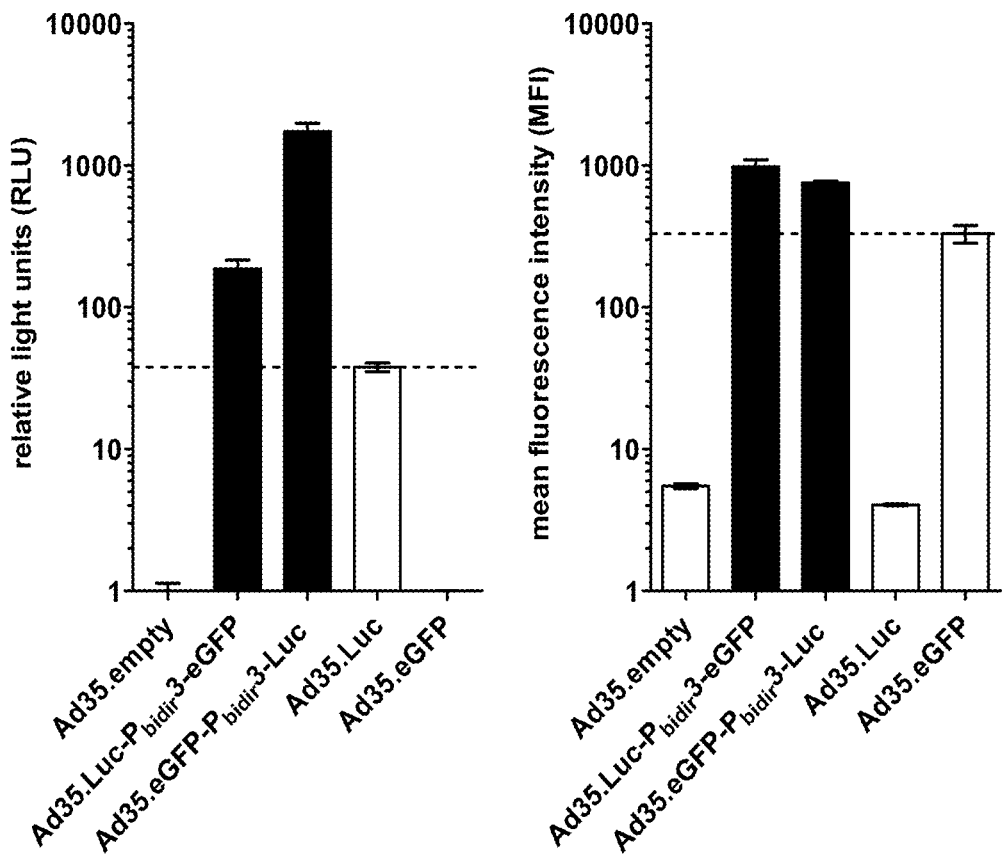
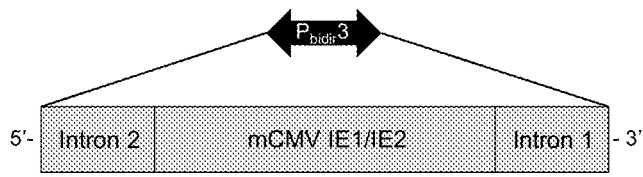
Fig. 5 - continued

(A) rHAd35: Bivalent E1-bidirectional design

(B)

eGFP-mCMV-Luc

Luc-mCMV-eGFP

MARV-mCMV-SEBOV

(C)

α-MARV

MARV-mCMV-SEBOV    E1.MARV

α-SEBOV

MARV-mCMV-SEBOV   E1.SEBOV

Fig. 7

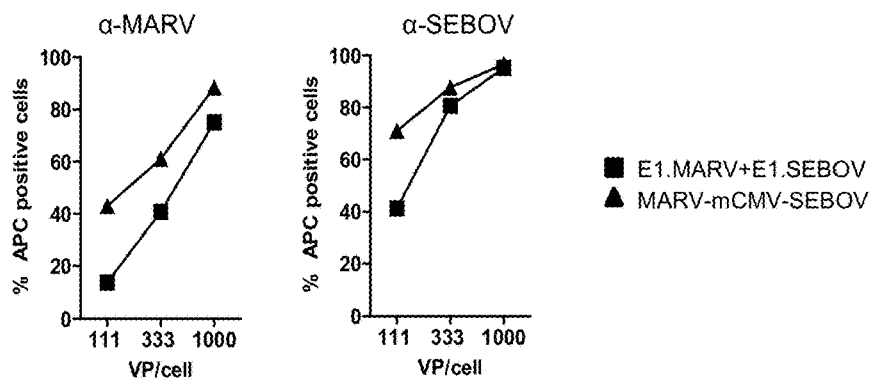
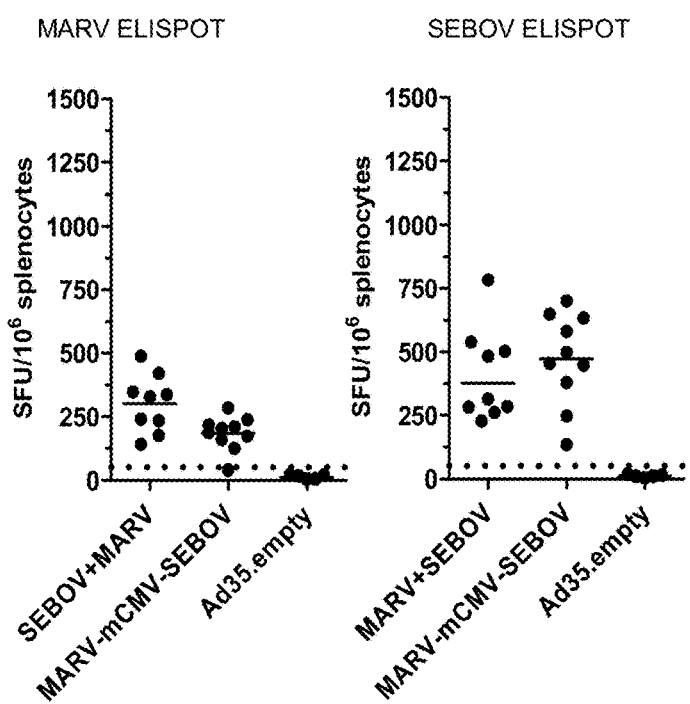# 
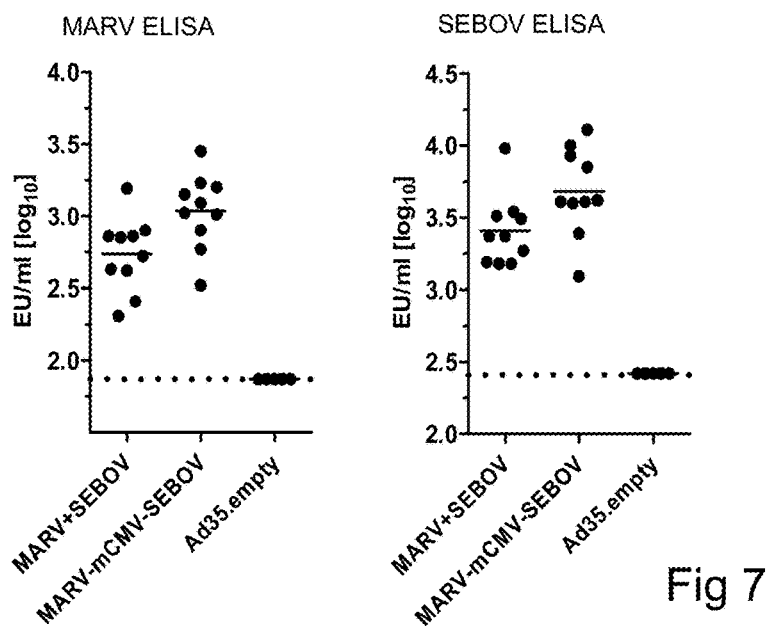
Fig 7 - continued

(A) rHAd26: Bivalent E1-bidirectional design

(B) MARV-mCMV-SEBOV

(C) α-MARV

MARV-mCMV-SEBOV    E1.MARV

α-SEBOV

MARV-mCMV-SEBOV    E1.SEBOV

α-MARV

α-SEBOV

% Ig positive cells

VP/cell

■ E1.MARV+E1.SEBOV
▲ MARV-mCMV-SEBOV

RECOMBINANT ADENOVIRUS EXPRESSING TWO TRANSGENES WITH A BIDIRECTIONAL PROMOTER

CROSS REFERENCE TO RELATED APPLICATIONS

This application is a Section 371 of International Application No. PCT/EP2016/057982, which was published in the English Language on Oct. 20, 2016, under International Publication No. WO2016/166088, which claims priority to U.S. Provisional Application No. 62/147,453, filed on Apr. 14, 2015 and European Patent Application No. 15163538.0, filed on Apr. 14, 2015. Each disclosure is incorporated herein by reference in its entirety.

GOVERNMENT RIGHTS

This invention was made with government support under Contract No. HHSN272200800056C by the National Institutes of Health. The government has certain rights in the invention.

REFERENCE TO SEQUENCE LISTING SUBMITTED ELECTRONICALLY

This application contains a sequence listing, which is submitted electronically via EFS-Web as an ASCII formatted sequence listing with a file name "688097-376US Sequence Listing" and a creation date of Sep. 19, 2017, and having a size of 6 kb. The sequence listing submitted via EFS-Web is part of the specification and is herein incorporated by reference in its entirety.

TECHNICAL FIELD

The invention relates to the field of medicine and to the field of gene delivery for applications in vaccination and gene therapy. More in particular, the invention relates to recombinant adenovirus and recombinant adenovirus vectors with bidirectional promoters for the expression of two transgenes.

BACKGROUND OF THE INVENTION

Recombinant human and animal adenoviruses are used extensively for their application in gene therapy and vaccination. For these applications, adenovirus vectors are used as carriers for a gene or genes of interest to be introduced into host cells. For example, adenovirus vectors can be used to express a gene or part thereof encoding a desired antigen to elicit an immune response.

First generation adenovirus vectors typically only included one transgene. Many strategies are published for these first generation vectors. The published strategies report the use of a variety of different adenovirus vectors and show that the transgene expression cassette can been placed in different regions of the adenovirus, for example in the E1 region, the E3 region, or between E4 and the right ITR.

For vaccine purposes, however, more than one antigen or the same antigen from several different strains is often required to achieve protection and broad coverage. Therefore, in certain cases, it is desirable to express at least two antigens from one adenoviral vector. Different approaches to encode two antigens in one adenoviral vector have been described.

In a first two antigen approach, one antigen expression cassette was placed in the E1 region and a second one was placed in the E3 region (e.g. (Vogels et al., 2007)). In a different two antigen approach, one antigen expression cassette was placed in E1 and a second one between E4 and the right ITR (e.g. (Holman et al., 2007; Pham et al., 2009; Schepp-Berglind et al., 2007)). In yet another two antigen approach, the two antigen expression cassettes were placed in the E1 region in a head-to-tail fashion using two different promoter sequences in an attempt to prevent genetic instability by recombination (e.g. (Belousova et al., 2006; Harro et al., 2009)).

Various other two antigen approaches have also been published for different viral vectors, for example with lentiviral vectors. Examples include use of bidirectional promoters or use of an internal ribosomal entry site (IRES) of positive-stranded RNA-viruses (e.g. derived from EMCV) to produce a single transcript that is translated into two proteins (e.g. (Amendola, Venneri, Biffi, Vigna, & Naldini, 2005; Na & Fan, 2010)). Other examples include utilizing the host cell splicing machinery or use of "cleavage" peptides derived from positive-stranded RNA viruses such as the foot-and-mouth-disease 2A sequence or equivalents from other viruses to produce a polyprotein that is cleaved into two proteins. According to published reports, all of these strategies can be equally useful and successful.

When two antigens are encoded in one adenoviral vector, several features of a monovalent vector should be maintained in order to make the multivalent vector both produceable and useful for vaccine purposes. Important features include genetic stability during upscaling, productivity of the vector at large scale, high level expression of both antigens, and immunogenicity of both antigens. However, for most of the published strategies the genetic stability and other features of the vectors have not been systematically analyzed.

Described herein are experimental results showing that approaches described in the prior art for expressing two antigens with a single recombinant adenovirus, lead to: a) reduced genetic stability in the upscaling process of the recombinant adenovirus (as can be mimicked by serial passaging in the helper cell line); b) reduced productivity of the recombinant adenovirus (decreasing the possibility to upscale the vectors to large purified batches); c) reduced expression of the antigens; and/or d) reduced immunogenicity of one or more of the antigens (in mouse model). These are clear disadvantages that do not support large scale use of recombinant adenovirus for expressing two antigens as described in the prior art.

Therefore, a need remains to provide a recombinant adenovirus that is genetically stable and that expresses two antigens in a manner in which the immunogenicity of both antigens is maintained.

SUMMARY OF THE INVENTION

The present invention provides methods of making and using recombinant adenovirus (rAd) and rAd vectors. The rAd and rAd vectors comprise two transgenes, wherein a first transgene is operably linked to a bidirectional mouse Cytomegalovirus (mCMV) promoter in one direction and a second transgene is operably linked to the bidirectional mCMV promoter in the other direction. The rAd of the present invention are genetically stable, with no deletion bands detected by PCR analysis up to passage 13 (p13), thus providing genetic stability that is comparable to rAd with only a single transgene. Furthermore, both transgenes are potently expressed based on FACS analysis of transgene expression and ELISPOT and ELISA analysis of the immunogenicity of the expressed antigens with regard to T-cell and B-cell responses. Thus, the rAd of the present invention with a bidirectional promoter were determined to be suitable for use in gene therapy and vaccine applications.

The general and preferred embodiments are defined, respectively, by the independent and dependent claims appended hereto, which for the sake of brevity are incorporated by reference herein. Other preferred embodiments, features, and advantages of the various aspects of the invention will become apparent from the detailed description below taken in conjunction with the appended drawing figures.

In one embodiment, the present invention provides a recombinant adenovirus comprising a bidirectional mouse CMV (mCMV) promoter operably linked to a first transgene in one direction and to a second transgene in the opposite direction.

In another embodiment, the present invention also provides a method of producing a recombinant adenovirus comprising a first and a second transgene, the method comprising: preparing a construct comprising a bidirectional mCMV promoter operably linked to a first transgene in one direction and to a second transgene in the opposite direction, and incorporating said construct into the genome of the recombinant adenovirus.

In certain embodiments, the recombinant adenovirus further comprises an intron positioned 3' of the promoter and 5' of the first transgene and an intron positioned 3' of the promoter and 5' of the second transgene.

In certain embodiments, the recombinant adenovirus has a deletion in the E1 region, and in certain embodiments comprises the bidirectional mCMV promoter and first and second transgenes and optionally the introns, in this E1 region.

In certain embodiments, the first and second transgene are different and at least one of them encodes an antigen. In certain embodiments both encode a different antigen.

In certain embodiments, the adenovirus is a human adenovirus serotype 35 or a human adenovirus serotype 26.

In another embodiment, the present invention also provides a method for expressing at least two transgenes in a cell, the method comprising providing a cell with a recombinant adenoviral vector according to the invention.

In another embodiment, the present invention also provides a method for inducing an immune response against at least two antigens, the method comprising administering to a subject a recombinant adenoviral vector according to the invention.

In another embodiment, the present invention also provides a recombinant DNA molecule comprising the genome of a recombinant adenovirus according to the invention.

In another embodiment, the present invention also provides a pharmaceutical composition comprising a recombinant adenovirus according to the invention and a pharmaceutically acceptable carrier or excipient. In certain embodiments, the pharmaceutical composition is a vaccine.

BRIEF DESCRIPTION OF THE DRAWINGS

FIG. 4: Design and testing of bivalent rAd35 vectors with an E1-E1 design. (A) Schematic design of bivalent vectors using E1-E1 approach: The E1 region contains two complete expression cassettes in a head to tail configuration, in which expression of gene 1 is driven by the human CMV promoter and expression of gene 2 is driven by a mCAG promoter that was chosen because of its heterologous sequence and comparable potency to the human CMV promoter. The two expression cassettes with gene 1 and gene 2 harbor heterologous poly-adenylation signals pA1 and pA2, respectively. (B) Shown are results for PCR analysis of the transgene region of rAd35.E1.mCAG.Luc-hCMV.eGFP and rAd35.E1.mCAG.MARV-hCMV.SEBOV. Numbers 1-5 represent DNA from five different plaques (viral populations) passaged to p13 in PER.C6® cells. P+ is the positive plasmid control showing the expected size of the PCR band and P− is a negative plasmid control showing the size of an expression cassette without an antigen. $H_2O$ is the water control of the PCR and M is the molecular weight markers. An asterisk indicates a PCR background band and an arrowhead indicates a deletion band. (C) Shown is a Western Blot to compare expression with bivalent rAd35.E1.mCAG-MARV.hCMV-SEBOV and monovalent vectors rAd35.E1.MARV or rAd35.E1.SEBOV. A549 cells were infected with rAd35.E1.mCAG-MARV.hCMV-SEBOV, rAd35.E1.MARV, or rAd35.E1.SEBOV at 1000, 2500 and 5000 VP/cell, harvested 48 hpi, and lysates were tested for expression of MARV and SEBOV proteins using MARV and SEBOV specific primary antibodies. (D) Shown are line graphs of the results with FACS staining for analysis of surface expression of MARV and SEBOV protein to compare expression from bivalent rAd35.E1.mCAG-MARV.hCMV-SEBOV and a mixture of monovalent vectors, rAd35.E1.MARV+rAd35.E1.SEBOV. A549 cells were infected with rAd35.MARV-F2A-SEBOV or a mix of rAd35.E1.MARV+rAd35.E1.SEBOV at 111, 333 and 1000 VP/cell. Presence of MARV and SEBOV on the surface of infected cells was analysed 48 hpi and % positive cells was plotted vs VP/cell. (E) Shown are results from an ELISPOT assay to evaluate the immunogenicity in mice at week 8 post immunization with bivalent rAd35.E1.mCAG-MARV.hCMV-SEBOV or a mix of monovalent vectors, rAd35.E1.MARV+rAd35.E1.SEBOV. Ad35.empty is the negative control. ELISPOT data is plotted as spot forming units (SFU)/$10^6$ splenocytes and corresponds to SEBOV and MARV specific T-cell responses with the different vectors. (F) Shown are results for an ELISA assay to measure the antibody responses (humoral response) against the MARV and SEBOV glycoproteins, expressed with bivalent rAd35.E1.mCAG-MARV.hCMV-SEBOV or a mix of monovalent vectors, rAd35.E1.MARV+rAd35.E1.SEBOV. Ad35.empy vector is the negative control. The ELISA data is presented in log scale as ELISA Units (EU)/ml. For both the ELISPOT and ELISA assays (E and F), groups of ten BALB/c mice were immunized intramuscularly (IM) with $1 \times 10^9$ VP of rAd35.E1.MARV-mCMV-SEBOV or with $1 \times 10^9$ VP rAd35.E1.MARV and $1 \times 10^9$ VP rAd35.E1.SEBOV. To account for the possible adjuvanting effect of the group receiving the total of $2 \times 10^9$ VP of single insert combination, $1 \times 10^9$ VP Ad35.empty vector was co-injected with the rAd35.E1.MARV-mCMV-SEBOV. As a negative control, two groups of five mice received a total of $2 \times 10^9$ VP Ad35.emtpy. Prior to vaccination, mice were also bled to generate naïve control serum (data not shown).

FIG. 6: Sequence of mCMV IE1/IE2 bidirectional promoter sequence (SEQ ID NO:2) with annotations for different functional segments. The direction and specific functional segments are indicated with arrows stacked on the sequence: the mCMV IE1/IE2 derived promoter sequence, MIE2 and MIE1 enhancers in both directions, the TATA box, and the transcription start site (TSS) flanked by a human ApoE1 derived intron sequence and a chimeric intron sequence.

FIG. 7: Design and testing of a bivalent rAd35 vector with an E1-bidirectional design. (A) Schematic design of rAd35 E1-bidirectional bivalent vectors: The E1 region contains a bidirectional expression cassette, in which both antigens are expressed under control of a bidirectional mouse CMV promoter using heterologous poly-adenylation signals $pA_1$ and $pA_2$. (B) Shown are results for PCR analysis of the transgene region of three different rAd35.E1.bidirectional vectors (rAd35.E1.eGFP-mCMV-Luc, (rAd35.E1.Luc-mCMV-eGFP, and rAd35.E1.MARV-mCMV-SEBOV. Numbers 1-5 represent DNA from five different plaques (viral populations) passaged to p13 in PER.C6® cells. P+ is the positive plasmid control showing the expected size of the PCR band and P− is a negative plasmid control showing the size of an expression cassette without an antigen. $H_2O$ is the water control of the PCR and M is the molecular weight markers. No deletion bands were detected in viral DNA from five different plaques (viral populations) passaged to p13 in PER.C6® cells for the rAd35 E1-bidirectional bivalent vectors. (C) Shown is a Western Blot to compare MARV and SEBOV expression with bivalent rAd35.E1.MARV-mCMV-SEBOV and monovalent vectors rAd35.E1.SEBOV and rAd35.E1.MARV. A549 cells were infected with indicated vectors at 1000, 2500 and 5000 VP/cell, harvested 48 hpi, and lysates were tested for expression of MARV and SEBOV proteins using MARV and SEBOV specific primary antibodies. (D) Shown are line graphs of the results with FACS staining for analysis of surface expression of MARV and SEBOV protein to compare expression from bivalent rAd35.E1.MARV-mCMV-SEBOV and a mixture of monovalent vectors rAd35.E1.MARV and rAd35.E1.SEBOV. A549 cells were infected with indicated vectors at 111, 333 and 1000 VP/cell. Presence of MARV and SEBOV on the surface of infected cells was analysed 48 hpi by FACS staining and % of positive cells is displayed. (E) Shown are results from an ELISPOT assay to evaluate the immunogenicity in mice at week 8 post immunization with bivalent rAd35.E1.MARV-mCMV-SEBOV or a mix of two monovalent vectors, rAd35.E1.MARV and rAd35.E1.SEBOV. Ad35.empy is the negative control. ELISPOT data is plotted as spot forming units (SFU)/$10^6$ splenocytes and corresponds to SEBOV and MARV specific T-cell responses with the different vectors. (F) Shown are results for an ELISA assay to measure the antibody responses (humoral response) against the MARV and SEBOV glycoproteins at week 8 post immunization in mice with bivalent rAd35.E1.MARV-mCMV-SEBOV or a mix of two monovalent vectors, rAd35.E1.MARV and rAd35.E1.SEBOV. Ad35.empy is the negative control. The ELISA data is presented in log scale as ELISA Units (EU)/ml. For both the ELISPOT and ELISA assays (E and F), groups of ten BALB/c mice were immunized intramuscularly (IM) with $1\times10^9$ VP of rAd35.E1.MARV-mCMV-SEBOV or with $1\times10^9$ VP rAd35.E1.MARV and $1\times10^9$ VP rAd35.E1.SEBOV. To account for the possible adjuvanting effect of the group receiving the total of $2\times10^9$ VP of single insert combination, $1\times10^9$ VP Ad35.empty vector was co-injected with the rAd35.E1.MARV-mCMV-SEBOV. As a negative control, two groups of five mice received a total of $2\times10^9$ VP Ad35.empty. Prior to vaccination, mice were also bled to generate naïve control serum (data not shown).

FIG. 8: Design and testing of a bivalent rAd26 vector with an E1-bidirectional design. (A) Schematic design of bivalent rAd26 vectors using E1-bidirectional approach. (B) Shown are results for PCR analysis of the transgene region of bivalent rAd26.E1.MARV-mCMV-SEBOV. Numbers 1-5 represent DNA from five different plaques (viral populations) passaged to p13 in PER.C6® cells. P+ is the positive plasmid control showing the expected size of the PCR band and P− is a negative plasmid control showing the size of an expression cassette without an antigen. $H_2O$ is the water control of the PCR and M is the molecular weight markers. (C) Shown is a Western Blot to compare MARV and SEBOV expression from bivalent rAd26.E1.MARV-mCMV-SEBOV and monovalent vectors rAd26.E1.SEBOV and rAd26.E1.MARV. A549 cells were infected with indicated vectors at 10 000, 25 000 and 50 000 VP/cell, harvested 48 hpi, and lysates were tested for expression of MARV and SEBOV proteins using MARV and SEBOV specific primary antibodies. (D) Shown are line graphs of the results with FACS staining for analysis of surface expression of MARV and SEBOV protein to compare expression from bivalent rAd26.E1.MARV-mCMV-SEBOV and a mixture of monovalent vectors rAd26.E1.MARV and rAd35.E1.SEBOV. A549 cells were infected with indicated vectors at 100 000, 20 000, 4000 and 800 VP/cell. Presence of MARV and SEBOV on the surface of infected cells was analysed 48 hpi by FACS staining. % of positive cells is displayed. (E) Shown are results from an ELISPOT assay to evaluate the immunogenicity in mice at week 8 post immunization with bivalent rAd26.E1.MARV-mCMV-SEBOV or a mix of two monovalent vectors, rAd26.E1.MARV and rAd26.E1.SEBOV. rAd26.empty is the negative control. ELISPOT data is plotted as spot forming units (SFU)/$10^6$ splenocytes and corresponds to SEBOV and MARV specific T-cell responses with the different vectors. (F) Shown are results for an ELISA assay to measure the antibody responses (humoral response) against the MARV and SEBOV glycoproteins at week 8 post immunization in mice with bivalent rAd26.E1.MARV-mCMV-SEBOV or a mix of two monovalent vectors, rAd26.E1.MARV and rAd26.E1.SEBOV. The rAd26.empy is the negative control. The ELISA data is presented in log scale as ELISA Units (EU)/ml. For both the ELISPOT and ELISA assays (E and F), groups of twelve BALB/c mice were immunized intramuscularly (IM) with $1\times10^9$ VP of rAd26.E1.MARV-mCMV-SEBOV or with $1\times10^9$ VP rAd26.E1.MARV and $1\times10^9$ VP rAd26.E1.SEBOV. To account for the possible adjuvanting effect of the group receiving the total of $2\times10^9$ VP of single insert combination, $1\times10^9$ VP rAd26.empty vector was co-injected with the rAd26.E1.MARV-mCMV-SEBOV. As a negative control, two groups of four mice received a total of $2\times10^9$ VP rAd26.empty. Prior to vaccination, mice were bled to generate naïve control serum (data not shown).

DETAILED DESCRIPTION OF THE INVENTION

Figure 1:
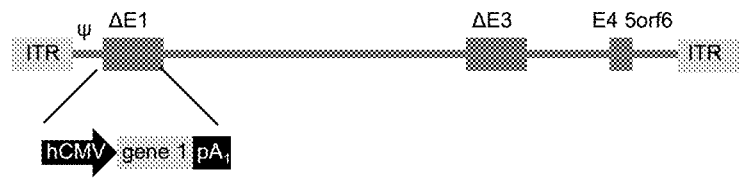
FIG. 1: Design and testing of monovalent rAd encoding a single transgene. (A) Schematic drawing of the genetic design of rAd with an expression cassette for a single gene in the E1 region and a Ψ packaging signal. (B) Schematic representation of the small scale genetic stability testing with PCR analysis for virus passaged in PER.C6® packaging cells. Passage p13 is 3 passages beyond commercial scale, depending on the details of the process. (C) Shown are results of E1 identity PCR analysis for 4 different viruses: rAd35.E1.EBOV, rAd35.E1.SEBOV, rAd35.E1.MARV and rAd26.E1.EBOV. Numbers 1-5 represent DNA from five different plaques (viral populations) passaged to pare bivalent rAd35.MARV-F2A-SEBOV to a mix of monovalent vectors, rAd35.E1.MARV+rAd35.E1.SEBOV. A549 cells were infected with rAd35.MARV-F2A-SEBOV or a mix of rAd35.E1.MARV+rAd35.E1.SEBOV at 111, 333 and 1000 VP/cell. Expression was analyzed 48 hpi and % positive cells was plotted vs VP/cell. (E) Shown are results from an ELISPOT assay to evaluate the immunogenicity in mice at week 8 post immunization with bivalent rAd35.MARV-F2A-SEBOV or a mix of monovalent vectors, rAd35.E1.MARV+rAd35.E1.SEBOV. rAd35.empy is the negative control. ELISPOT data is plotted as spot forming units (SFU)/$10^6$ splenocytes and corresponds to SEBOV and MARV specific T-cell responses with the different vectors. (F) Shown are results for an ELISA assay to measure the antibody responses (humoral response, B-cell response) against the MARV and SEBOV glycoproteins, expressed with bivalent rAd35.MARV-F2A-SEBOV or a mix of monovalent vectors, rAd35.E1.MARV and rAd35.E1.SEBOV (MARV+SEBOV). rAd35.empy is the negative control. The ELISA data is presented in log scale as ELISA Units (EU)/ml. For both the ELISPOT and ELISA assays (E and F), groups of ten BALB/c mice were immunized intramuscularly (IM) with $1 \times 10^9$ VP of rAd35.E1.MARV-mCMV-SEBOV or with $1 \times 10^9$ VP rAd35.E1.MARV and $1 \times 10^9$ VP rAd35.E1.SEBOV. To account for the possible adjuvanting effect of the group receiving the total of $2 \times 10^9$ VP of single insert combination, $1 \times 10^9$ VP Ad35.empty vector was co-injected with the rAd35.E1.MARV-mCMV-SEBOV. As a negative control, two groups of five mice received a total of $2 \times 10^9$ VP Ad35.emtpy. Prior to vaccination, mice were also bled to generate naïve control serum (data not shown).
Figure 1:
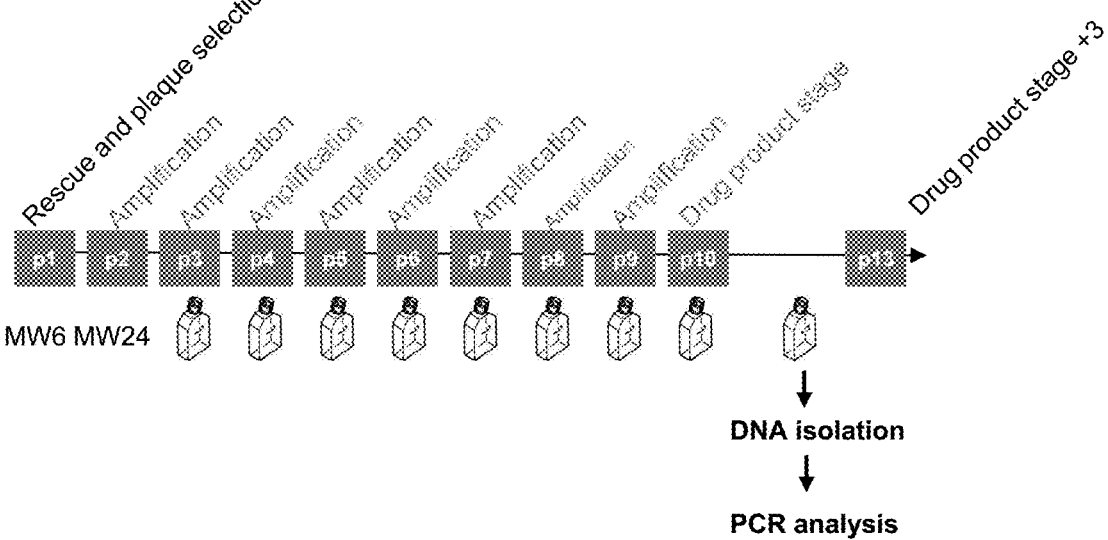
Figure 1:
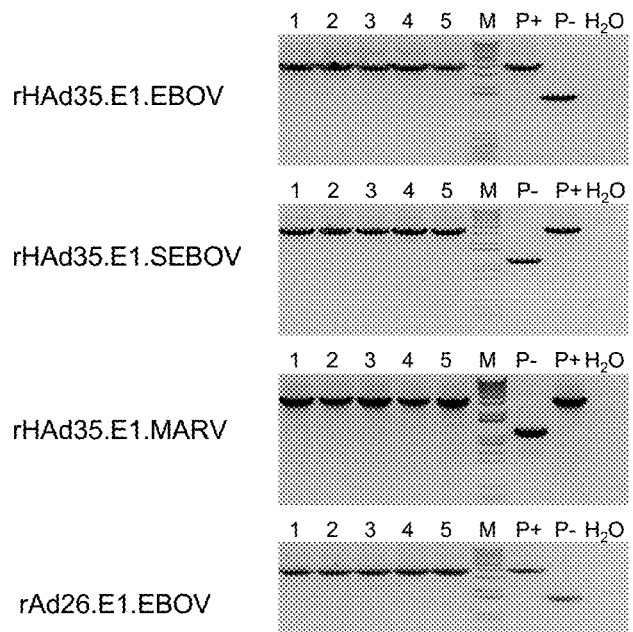

Described herein are experimental results showing that approaches described in the prior art for expressing two transgenes from one recombinant adenovirus (rAd) lead to genetic instability of the rAd and/or reduced transgene expression compared to rAd with single transgenes expressing the same antigens. After testing several different new strategies to solve these problems, a novel solution was identified using rAd vectors with two transgenes placed under control of a bidirectional mouse Cytomegalovirus (mCMV) promoter. The rAd of the present invention are superior to the bivalent rAd that have been described in the prior art. The bivalent rAd with a bidirectional mCMV are genetically stable, with no deletion bands detected by PCR analysis up to passage 13 (p13), thus providing genetic stability that is comparable to rAd with only a single transgene. Furthermore, both transgenes are potently expressed based on Western Blot and FACS analysis of transgene expression and ELISPOT and ELISA analysis of the immunogenicity of the expressed antigens with regard to T-cell and B-cell responses. Thus, the rAd of the present invention with a bidirectional promoter were determined to be suitable for use in gene therapy and vaccine applications.

The present invention therefore relates to the rAd and the rAd vectors, methods of making and using the rAd and rAd vectors, wherein the rAd and rAd vectors comprise a bidirectional mCMV promoter and two transgenes, wherein a first transgene is operably linked to the bidirectional mCMV promoter in one direction and a second transgene is operably linked to the bidirectional mCMV promoter in the other direction.

The rAd of the present invention can be produced in large amounts, or batches. A 'batch' of rAd is a composition that has been produced in one production run in a single production vessel, or alternatively it can refer to the plurality of rAd particles in a composition that is present in a single container (e.g., bioreactor, bag, flask, bottle, multi-dose vial, single-dose vial, syringe, etc). A batch of rAd according to the invention or a composition comprising rAd according to the invention preferably comprises at least $10^7$ rAd particles, and in certain embodiments comprises at least $10^8$, $10^9$, $10^{10}$, $10^{11}$, $10^{12}$, $10^{13}$, $10^{14}$, $10^{15}$, $10^{16}$, $10^{17}$, $10^{18}$, or more rAd particles, up to $10^{20}$ rAd particles (e.g. as produced in a large scale bioreactor in a single production run). A batch or composition may or may not comprise further relevant components besides the rAd.

The term 'recombinant' for a recombinant adenovirus, as used herein implicates that it has been modified by the hand of man as opposed to wild-type adenoviruses, e.g. it comprises a heterologous gene, genes, or parts thereof and a bidirectional mCMV promoter.

Sequences herein are provided in the 5' to 3' direction, as is customary in the art.

An "adenovirus capsid protein" refers to a protein on the capsid of an adenovirus that is involved in determining the serotype and/or tropism of a particular adenovirus. Adenoviral capsid proteins typically include the fiber, penton and/or hexon proteins. A rAd of (or 'based upon') a certain serotype according to the invention typically comprises fiber, penton and/or hexon proteins of that certain serotype, and preferably comprises fiber, penton and hexon protein of that certain serotype. These proteins are typically encoded by the genome of the rAd. A rAd of a certain serotype may optionally comprise and/or encode other proteins from other adenovirus serotypes.

A rAd is 'based upon' an adenovirus as used herein, by derivation from the wild type, at least in sequence. This can be accomplished by molecular cloning, using the wild type genome or parts thereof as starting material. It is also possible to use the known sequence of a wild type adenovirus genome to generate (parts of) the genome de novo by DNA synthesis, which can be performed using routine procedures by service companies having business in the field of DNA synthesis and/or molecular cloning (e.g. GeneArt, GenScripts, Invitrogen, Eurofins). Thus, as a non-limiting example, a rAd that comprises hexon, penton and fiber of Ad35 is considered a rAd based upon Ad35, etc.

The vectors of the present invention are referred to as rAd vectors. The preparation of rAd vectors is well known in the art.

In certain embodiments, a rAd vector according to the invention is deficient in at least one essential gene function of the E1 region, e.g. the E1a region and/or the E1b region, of the adenoviral genome that is required for viral replication. In certain embodiments, an adenoviral vector according to the invention is deficient in at least part of the non-essential E3 region. In certain embodiments, the vector is deficient in at least one essential gene function of the E1 region and at least part of the non-essential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region).

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, 6,113,913, and 8,932,607, and Thomas Shenk, "Adenoviridae and their Replication" M. S. Horowitz, "Adenoviruses", Chapters 67 and 68, respectively, in *Virology*, B. N. Fields et al., eds., 3d ed., Raven Press, Ltd., New York (1996), and other references mentioned herein. Typically, construction of adenoviral vectors involves the use of standard molecular biological techniques, such as those described in, for example, Sambrook et al., *Molecular Cloning, a Laboratory Manual*, 2d ed., Cold Spring Harbor Press, Cold Spring Harbor, N.Y. (1989), Watson et al., *Recombinant DNA*, 2d ed., Scientific American Books (1992), and Ausubel et al., *Current Protocols in Molecular Biology*, Wiley Interscience Publishers, NY (1995), and other references mentioned herein.

An adenovirus according to the invention belongs to the family of the Adenoviridae and preferably is one that belongs to the genus Mastadenovirus. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu; in the present invention a human adenovirus is meant if referred to Ad without indication of species, e.g. the brief notation "Ad5" means the same as HAdV5, which is human adenovirus serotype 5), or a simian adenovirus such as chimpanzee or gorilla adenovirus (ChAd, AdCh, or SAdV).

Most advanced studies have been performed using human adenoviruses, and human adenoviruses are preferred according to certain aspects of the invention. In certain preferred embodiments, the recombinant adenovirus according to the invention is based upon a human adenovirus. In preferred embodiments, the recombinant adenovirus is based upon a human adenovirus serotype 5, 11, 26, 34, 35, 48, 49 or 50. According to a particularly preferred embodiment of the invention, an adenovirus is a human adenovirus of one of the serotypes 26, 35. An advantage of these serotypes is a low seroprevalence and/or low pre-existing neutralizing antibody titers in the human population. Preparation of rAd26 vectors is described, for example, in WO 2007/104792 and in (Abbink et al., 2007). Exemplary genome sequences of Ad26 are found in GenBank Accession EF 153474 and in SEQ ID NO:1 of WO 2007/104792. Preparation of rAd35 vectors is described, for example, in U.S. Pat. No. 7,270, 811, in WO 00/70071, and in (Vogels et al., 2003). Exemplary genome sequences of Ad35 are found in GenBank Accession AC_000019 and in FIG. 6 of WO 00/70071.

Simian adenoviruses generally also have a low seroprevalence and/or low pre-existing neutralizing antibody titers in the human population, and a significant amount of work has been reported using chimpanzee adenovirus vectors (e.g. U.S. Pat. No. 6,083,716; WO 2005/071093; WO 2010/086189; WO 2010085984; (Bangari & Mittal, 2006; Cohen et al., 2002; Farina et al., 2001; Kobinger et al., 2006; Lasaro & Ertl, 2009; Tatsis et al., 2007). Hence, in other preferred embodiments, the recombinant adenovirus according to the invention is based upon a simian adenovirus, e.g. a chimpanzee adenovirus. In certain embodiments, the recombinant adenovirus is based upon simian adenovirus type 1, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P.

The sequences of most of the human and non-human adenoviruses mentioned above are known, and for others can be obtained using routine procedures.

A recombinant adenovirus according to the invention may be replication-competent or replication-deficient.

In certain embodiments, the adenovirus is replication deficient, e.g. because it contains a deletion in the E1 region of the genome. A "deletion in the E1 region" means a deletion in this region as compared to a wild-type adenovirus, and means a deletion in at least one of the E1A, E1B 55K or E1B 21K coding regions, preferably a deletion of E1A, E1B 55K and E1B21K coding regions. As known to the skilled person, in case of deletions of essential regions from the adenovirus genome, the functions encoded by these regions have to be provided in trans, preferably by the producer cell, i.e. when parts or whole of E1, E2 and/or E4 regions are deleted from the adenovirus, these have to be present in the producer cell, for instance integrated in the genome thereof, or in the form of so-called helper adenovirus or helper plasmids. The adenovirus may also have a deletion in the E3 region, which is dispensable for replication, and hence such a deletion does not have to be complemented.

A producer cell (sometimes also referred to in the art and herein as 'packaging cell' or 'complementing cell' or 'host cell') that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g. 911 or PER.C6 cells (see U.S. Pat. No. 5,994,128), E1-transformed amniocytes (See EP patent 1230354), E1-transformed A549 cells (see e.g. WO 98/39411, U.S. Pat. No. 5,891,690), GH329:HeLa (Gao, Engdahl, & Wilson, 2000), 293, and the like. In certain embodiments, the producer cells are for instance HEK293 cells, or PER.C6 cells, or 911 cells, or IT293SF cells, and the like. For E1-deficient adenoviruses that are not derived from subgroup C or E adenoviruses, it is preferred to exchange the E4-orf6 coding sequence of the non-subgroup C or E adenovirus with the E4-orf6 of an adenovirus of subgroup C such as Ad5. This allows propagation of such adenoviruses in well-known complementing cell lines that express the E1 genes of Ad5, such as for example 293 cells or PER.C6 cells (see, e.g. (Havenga et al., 2006); WO 03/104467, incorporated in its entirety by reference herein).

In alternative embodiments, there is no need to place a heterologous E4orf6 region (e.g. of Ad5) in the adenoviral vector, but instead the E1-deficient non-subgroup C or E vector is propagated in a cell line that expresses both E1 and a compatible E4orf6, e.g. the 293-ORF6 cell line that expresses both E1 and E4orf6 from Ad5 (see e.g. (Brough, Lizonova, Hsu, Kulesa, & Kovesdi, 1996) describing the generation of the 293-ORF6 cells; (Abrahamsen et al., 1997; Nan et al., 2003) each describing generation of E1 deleted non-subgroup C adenoviral vectors using such a cell line).

Alternatively, a complementing cell that expresses E1 from the serotype that is to be propagated can be used (see e.g. WO 00/70071, WO 02/40665).

For subgroup B adenoviruses, such as Ad35, having a deletion in the E1 region, it is preferred to retain the 3' end of the E1B 55K open reading frame in the adenovirus, for instance the 166 bp directly upstream of the pIX open reading frame or a fragment comprising this such as a 243 bp fragment directly upstream of the pIX start codon (marked at the 5' end by a Bsu36I restriction site in the Ad35 genome), since this increases the stability of the adenovirus because the promoter of the pIX gene is partly residing in this area (see, e.g. (Havenga et al., 2006); WO 2004/001032, incorporated by reference herein).

"Heterologous nucleic acid" (also referred to herein as 'transgene') in adenoviruses of the invention is nucleic acid that is not naturally present in the adenovirus. It is introduced into the adenovirus for instance by standard molecular biology techniques. It may in certain embodiments encode a protein of interest or part thereof. It can for instance be cloned into a deleted E1 or E3 region of an adenoviral vector. In preferred embodiments of the invention, the expression cassette with the two transgenes under control of the bidirectional mCMV promoter is placed into the E1 region of the adenoviral genome. A transgene is generally operably linked to expression control sequences. This can for instance be done by placing the nucleic acid encoding the transgene(s) under the control of a promoter. Many promoters can be used for expression of a transgene(s), and are known to the skilled person.

As used herein, the terms "promoter" or "promoter region" or "promoter element" are used interchangeably, and refer to a segment of a nucleic acid sequence, typically but not limited to DNA, that controls the transcription of the nucleic acid sequence to which it is operatively linked. The promoter region includes specific sequences that are sufficient for RNA polymerase recognition, binding and transcription initiation. In addition, the promoter region can optionally include sequences which modulate this recognition, binding and transcription initiation activity of RNA polymerase. These sequences may be cis-acting or may be responsive to trans-acting factors. Promoters, depending upon the nature of the regulation may be constitutive or regulated. The current invention uses the bidirectional mouse CMV promoter (mCMV) to direct transcription of two different transgenes in a bidirectional fashion.

Further regulatory sequences may also be added. The term "regulatory sequence" is used interchangeably with "regulatory element" herein and refers to a segment of nucleic acid, typically but not limited to DNA, that modulate the transcription of the nucleic acid sequence to which it is operatively linked, and thus acts as a transcriptional modulator. A regulatory sequence often comprises nucleic acid sequences that are transcription binding domains that are recognized by the nucleic acid-binding domains of transcriptional proteins and/or transcription factors, enhancers or repressors etc. For example, a regulatory sequence could include one or more tetracycline operon operator sequences (tetO), such that expression is inhibited in the presence of the tetracycline operon repressor protein (tetR). In the absence of tetracycline, the tetR protein is able to bind to the tetO sites and repress transcription of a gene operably linked to the tetO sites. In the presence of tetracycline, however, a conformational change in the tetR protein prevents it from binding to the operator sequences, allowing transcription of operably linked genes to occur. In certain embodiments, rAd of the present invention can optionally include tetO operatively linked to a bidirectional mouse CMV promoter, such that expression of one or more transgenes is inhibited in rAd that are produced in the producer cell line in which tetR protein is expressed. Subsequently, expression would not be inhibited if the rAd is introduced into a subject or into cells that do not express the tetR protein (see e.g., international patent application WO 07/073513). In certain other embodiments, rAd of the present invention can optionally include a cumate gene-switch system, in which regulation of expression is mediated by the binding of the repressor (CymR) to the operator site (CuO), placed downstream of the promoter (see e.g., (Mullick et al., 2006)).

As used herein, the term "repressor," refers to entities (e.g., proteins or other molecules) having the capacity to inhibit, interfere, retard and/or repress the production of heterologous protein product of a recombinant expression vector. For example, by interfering with a binding site at an appropriate location along the expression vector, such as in an expression cassette. Examples of repressors include tetR, CymR, the lac repressor, the trp repressor, the gal repressor, the lambda repressor, and other appropriate repressors known in the art.

Figure 8:
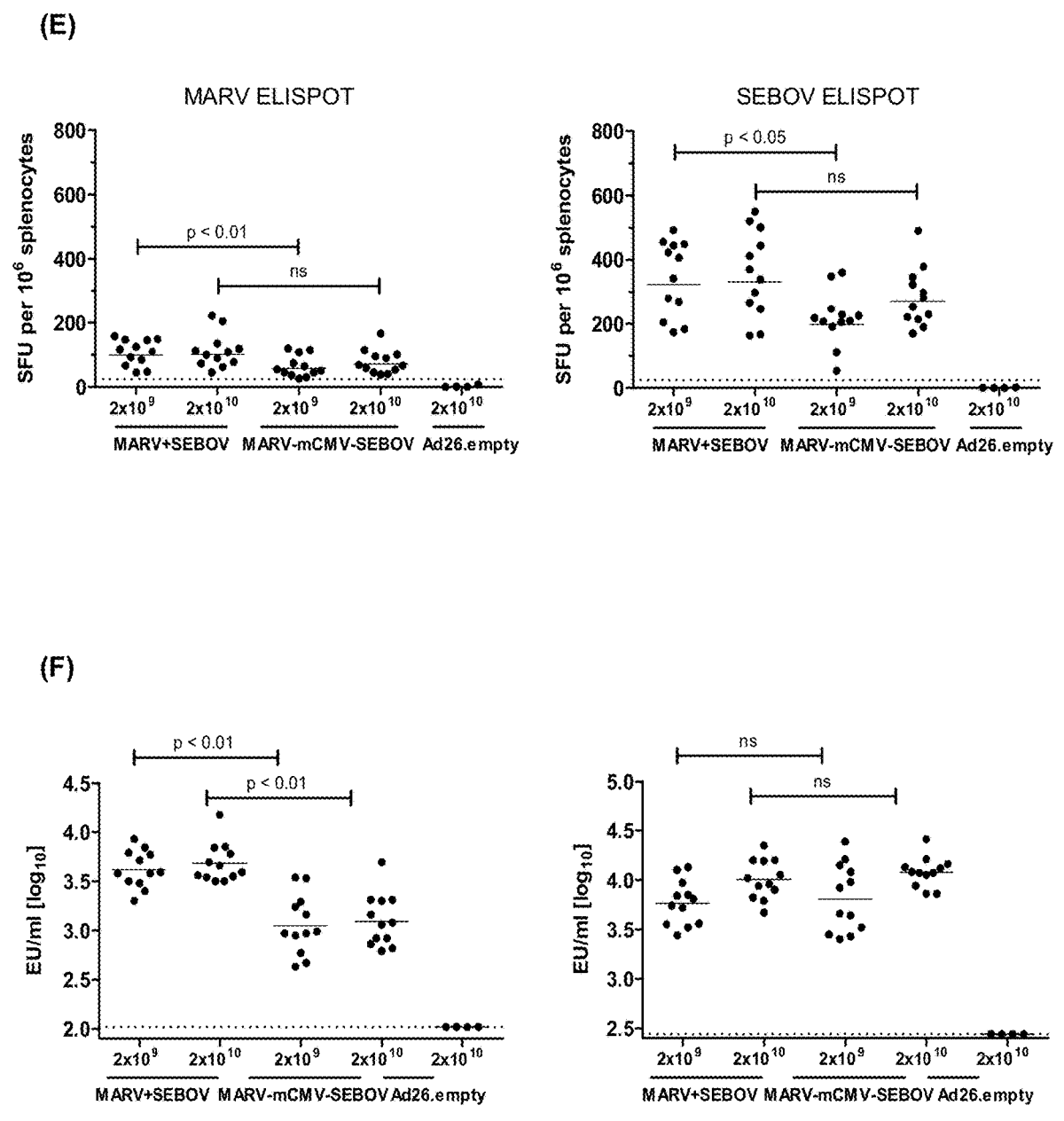

The recombinant adenoviruses of the present invention comprise a bidirectional mouse CMV (mCMV) promoter operably linked to a first transgene in one direction and to a second transgene in the opposite direction. The bidirectional mCMV promoter has been described in detail in European Pat. No. EP1601776, and comprises the mCMV immediate early 1 promoter (IE1) in one direction and the mCMV immediate early 2 promoter (IE2) in opposite direction. It may further comprise enhancers, such as the natural or other enhancers. The natural enhancer for the bidirectional mCMV promoter comprises a major immediate early 1 (MIE1) enhancer and a MIE2 enhancer. Enhancers may also be exchanged for other enhancers that are not naturally present in the mCMV IE region, and/or placed in other positions. Preferably, the enhancer sequences for the promoter in the first direction and the promoter in the other direction do not overlap. The promoter is in a bidirectional architecture, which means that both promoters (i.e. IE1 and IE2 promoters, together constituting the mCMV IE bidirectional promoter) drive expression in opposite orientation, and outward from the center of the two promoters towards the ends of the adenoviral genome, as understood by one skilled in the art. The bidirectional promoter thus will drive expression of the first transgene towards a first end of the adenoviral genome and of the second transgene towards the other end of the adenoviral genome. Schematic representations of rAd and rAd vector constructs of the present invention are provided in FIGS. 5, 7, and 8. The annotated sequence of a representative bidirectional mCMV promoter is provided in FIG. 6. Representative sequences are provided for a mCMV bidirectional promoter sequence including introns (SEQ ID NO:1) and a mCMV promoter excluding introns (SEQ ID NO:2). The skilled person will be aware that the mCMV IE1 and IE2 promoters are the active promoter sequences (see, for example, European Pat. No. EP1601776), and that mutations can be made in the provided sequences and can be tested for promoter activity by routine methods. Typically, a sequence having at least 90% identity with the indicated promoter sequences (not including the intron sequences in case intron sequences would be present) will still have functional activity and hence will be considered a bidirectional mCMV promoter. Thus, the bidirectional mCMV promoter of the present invention preferably has at least 90%, 91%, 92%, 93%, 94%, 95%, 96%, 97%, 98%, or 99% identity to the indicated promoter sequences (outside the intron sequences in case intron sequences would be present). In certain embodiments, the bidirectional mCMV promoter is 100% identical to the sequences disclosed herein.

The terms "operably linked", or "operatively linked" are used interchangeably herein, and refer to the functional relationship of the nucleic acid sequences with regulatory sequences of nucleotides, such as promoters, enhancers, transcriptional and translational stop sites, and other signal sequences and indicates that two or more DNA segments are joined together such that they function in concert for their intended purposes. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined.

The mCMV IE1 part of the bidirectional promoter provides stronger expression than the mCMV IE2 part of the bidirectional promoter (about 10× expression level difference, as tested for luciferase), and therefore the transgene for which the highest expression is desired can be placed under control of the mCMV IE1 part of the bidirectional promoter. However, with expression controlled by either part of the bidirectional promoter the transgene is potently expressed. As used herein, "potently expressed" or "potent expression" mean that the expression, as measured by different protein detection techniques such as Western Blot or FACS analysis, is comparable to or even better than expression from monovalent rAd expressing a single antigen under the control of an hCMV promoter. For example, the expression level as determined by FACS analysis of both antigens from the bidirectional mCMV promoter of the present invention is preferably at least 60%, 70%, 80%, 90%, or 95% of the antigen expression level from a monovalent rAd with an hCMV promoter. In certain embodiments, the expression level of both antigens from the bidirectional mCMV is 100% of the antigen expression level from a monovalent rAd with an hCMV promoter. Furthermore, it is known from rAd expressing a single antigen under the control of an hCMV promoter that the expression is sufficient to generate significant T-cell and B-cell immune responses. Therefore, potent expression of two transgenes expressed by an mCMV bidirectional promoter of the present invention is expected to generate a significant T-cell and B-cell immune response to both transgenes. For example, if the two transgenes encode antigens to elicit an immune response when administered to a subject, potent expression will generate a measurable immune response against both antigens and that immune response will preferably be the same or better than the immune response generated by an rAd with a single transgene expressing a single antigen under the control of a hCMV promoter.

The terms "coding sequence", sequence encoding, or "encoding" are used interchangeably herein, and refer to the nucleic acid sequence which is transcribed (DNA) and translated (mRNA) into a polypeptide in vitro or in vivo when operably linked to appropriate regulatory sequences.

A polyadenylation signal, for example the bovine growth hormone polyA signal (U.S. Pat. No. 5,122,458), may be present behind the transgenes. Preferably, each transgene has a polyA signal, and preferably the polyA signal for the first transgene is different from the polyA signal for the second transgene. In one embodiment, a first polyA signal is an SV40 polyA signal, and a second polyA signal is the bovine growth hormone polyA signal.

In preferred embodiments, a sequence comprising an intron is positioned downstream (3') of the promoter and upstream (5') of the first transgene, and a further sequence comprising an intron is positioned downstream of the promoter and upstream of the second transgene. These introns may be the same or different. An intron as used herein has the normal function and structure as known in the art, and is a polynucleotide sequence in a nucleic acid that does not encode information for protein synthesis and is removed before translation of messenger RNA, by a process known as splicing. An intron comprises a splice donor site (5' end of the intron, usually a GU sequence) and a splice acceptor site (3' end of the intron, usually a GA sequence). A schematic representation of the architecture of the constructs according to the invention comprising introns is provided in FIG. 5D. A representative sequence for a mCMV bidirectional promoter sequence including introns is provided as SEQ ID NO:1. A representative sequence for a mCMV bidirectional promoter sequence excluding introns is provided as SEQ ID NO:2. Any intron can be used according to the invention, and it is preferred to use relatively short introns in order to not take up too much space in a viral vector, so that more space remains for the transgenes in the recombinant adenovirus. It is preferred to use a first intron on one side of the bidirectional promoter and a second, different intron on the other side of the bidirectional promoter, i.e. each transgene is preceded by a different intron sequence. In certain embodiments, a first intron is a chimeric intron, e.g. having SEQ ID NO:3. In certain embodiments, a further intron is a human ApoAl intron, e.g. having SEQ ID NO:4. The skilled person is aware that many different introns are available and can be used. It is known that introns increase protein expression, in particular in vivo. An advantage of the embodiments of the invention where introns are present is thus high expression of the transgenes, which is very useful for immunogenicity or for gene therapy.

One of the exemplified parameters in the experiments described herein is immunogenicity, which is relevant for antigens in a vaccine application. However, it will be immediately clear to the skilled person that transgene expression levels can also be relevant for transgenes for which an immune response is not the primary goal, e.g. for transgenes that are used in gene therapy purposes. Hence, the invention can be practiced with any combination of transgenes for which expression from a single recombinant adenoviral vector is desired. Therefore, the identity of the transgene is not material for the instant invention, which is suitable for adenoviruses comprising any transgene. Suitable transgenes are well known to the skilled person, and for instance may include transgene open reading frames, for instance open reading frames coding for polypeptides that have a therapeutic effect, e.g. for gene therapy purposes, or polypeptides against which an immune response is desired when the rAd vector is used for vaccination purposes. Particularly preferred heterologous nucleic acids are genes of interest encoding antigenic determinants towards which an immune response needs to be raised. Such antigenic determinants are also typically referred to as antigens. When the recombinant adenovirus is administered to a subject, an immune response will be raised against the antigen(s). Any desired antigen can be encoded by the adenovirus vector. In typical embodiments according to the invention, antigens are peptides, polypeptides or proteins from organisms that may cause a disease or condition. Therefore, in a further preferred embodiment, said heterologous nucleic acid of interest encodes an immunogenic (or antigenic) determinant. More preferably, said immunogenic determinant is an antigen from a bacterium, a virus, yeast or a parasite. The diseases caused by such organisms are generally referred to as 'infectious disease' (and are thus not limited to organisms that 'infect' but also include those that enter the host and cause a disease). So-called 'self-antigens', e.g. tumour antigens, also form part of the state of the art, and may be encoded by heterologous nucleic acids in the recombinant adenoviruses according to the present invention. Non-limiting examples from which the antigenic determinants (or antigens) are taken are malaria-causing organisms, such as *Plasmodium falciparum*, tuberculosis-causing organism such as *Mycobacterium tuberculosis*, yeasts, or viruses. In other preferred embodiments, antigens from viruses such as flaviviruses (e.g., West Nile Virus, Hepatitis C Virus, Japanese Encephalitis Virus, Dengue Virus), Ebola virus, Human Immunodeficiency Virus (HIV), and Marburg virus may be used in compositions according to the present invention. In one embodiment, said antigen is the CS protein or immunogenic part thereof from *P. falciparum* (for examples of adenovirus vectors encoding CS, see e.g. (Havenga et al., 2006; Ophorst et al., 2006); WO 2004/055187, all incorporated in their entirety by reference herein). In another embodiment, the antigenic determinant is a protein of one antigen-, or a fusion protein of several antigens from *M. tuberculosis*, such as the Ag85A, Ag85B and/or the TB10.4 proteins or immunogenic part(s) thereof (see for the construction and production of such TB vaccine viruses e.g. WO 2006/053871, incorporated by reference herein). In yet another embodiment, said antigenic determinant is a viral glycoprotein or immunogenic part thereof, such as GP from a filovirus, such as Ebola virus or Marburg virus (e.g. (Geisbert et al., 2011; Sullivan et al., 2006; Sullivan et al., 2003). In yet further embodiments, said immunogenic determinant is from an HIV protein such as gag, pol, env, nef, or variants thereof (for examples of adenovirus based HIV vaccines, see e.g. WO 2009/026183, WO 2010/096561, WO 2006/120034, WO 02/22080, WO 01/02607). In other embodiments, said antigenic determinant is a HA, NA, M, or NP protein, or immunogenic part of any of these, from influenza virus (e.g. (Hu et al., 2011; Zhou et al., 2010); review by (Vemula & Mittal, 2010)). In other embodiments, the antigenic determinant is a HA protein or immunogenic part thereof from a measles virus (e.g. WO 2004/037294). In other embodiments, the antigenic determinant is rabies virus glycoprotein (e.g. (Zhou, Cun, Li, Xiang, & Ertl, 2006)). In further embodiments, the antigen is from a respiratory syncytial virus (RSV), e.g. RSV F protein (see e.g. WO 2013/139911 and WO 2013/139916), or RSV G protein, or both, or other RSV proteins. In other embodiments, the antigen is from another virus such as human papillomavirus or other viruses, etc. The recombinant adenovirus may encode two different antigens from the same organism. The recombinant adenovirus may also encode combinations of antigens from different organisms, e.g. a first antigen from a first organism and second antigen from a second organism. It is also possible to encode an antigen and for instance an adjuvant into the same adenovirus, e.g. an antigen and a Toll-Like-Receptor (TLR) agonist, such as a TLR3 agonist, such as dsRNA or a mimetic thereof or the like (e.g. WO 2007/100908). In certain embodiments, the recombinant adenovirus encodes two different antigens, each under control of the bidirectional mCMV promoter. In other embodiments, the recombinant adenovirus encodes an antigen and an immune modulator, each under control of the bidirectional mCMV promoter. In certain embodiments, further heterologous sequences or transgenes may be present in the recombinant adenovirus, besides the first and second transgene that are under control of the bidirectional mCMV promoter.

The invention also provides a method for producing a genetically stable recombinant adenovirus comprising a first and a second transgene that each are potently expressed when the adenovirus infects a target cell, the method comprising: preparing a construct comprising a bidirectional mCMV promoter operably linked to a first transgene in one direction and to a second transgene in the opposite direction, and incorporating said construct into the genome of the recombinant adenovirus. The preparation of the construct as such encompasses the use of standard molecular cloning methods (see e.g. (Holterman et al., 2004; Lemckert et al., 2006; Vogels et al., 2003); Sambrook, Fritsch and Maniatis, Molecular Cloning: A Laboratory Manual, 2nd edition, 1989; Current Protocols in Molecular Biology, Ausubel F M, et al, eds, 1987; the series Methods in Enzymology (Academic Press, Inc.); PCR2: A Practical Approach, MacPherson M J, Hams B D, Taylor G R, eds, 1995), as known to the skilled person and routinely performed in the field of recombinant adenovirus technology, and exemplified herein. The bidirectional mCMV promoter has the features as described above, and can be obtained by routine methods (see e.g. European Pat. No. EP1601776). For convenience, the skilled person may manipulate the adenovirus genome by cloning into smaller fragments, e.g. a first part for the left part of the genome up to the E1 region for easy manipulation and introduction of the transgenes in plasmid form and a second, larger, part for the remainder of the genome that can upon recombination with the first part result in a complete adenovirus genome (see e.g. WO 99/55132).

The rAd of the present invention has the advantage that it can express two transgenes and remains genetically stable, unlike adenoviruses prepared by the various alternative approaches for expressing two transgenes that are provided in the prior art. Thus, the bidirectional mCMV promoter solves the problem of genetic instability of adenoviruses that express two transgenes.

To measure genetic stability, rAd are rescued and passaged in an appropriate cell line, e.g., helper cell line PER.C6®. Viral DNA is isolated at certain passage numbers and the integrity of the rAd genome can be analyzed by one or more of the following: PCR analysis for presence or absence of deletion bands, restriction digests of the rAd genome for presence or absence of differences in restriction fragments, and/or sequencing of the rAd genome or of PCR-products of the rAd genome for presence or absence of mutations in the rAd sequences. With regard to the rAd of the present invention, "genetically stable" means that the nucleotide sequence does not change from the plasmids used for generation of the rAd to later production stages of the rAd, such that rAd expressing two transgenes has the same genetic stability as a comparable rAd with a single transgene (behind a hCMV promoter) as suitable for large scale batch productions. For example, PCR analysis using primers flanking the expression cassette does not show deletion fragments (bands) compared to earlier passage numbers of the rAd or the starting material and/or sequencing the PCR product of the E1, E3 and E4 regions confirms that the nucleotide sequence does not change. Genetic stability is thoroughly assessed in this study compared to other testing methods such as test digestions on a single produced virus batch. Sensitivity of the assay is increased by the following means: several viral populations (plaques) are isolated and subjected to extended passaging. The extended passaging, combined with a PCR analysis using primers flanking the expression cassette allows for detection of a small proportion of deletion mutants in the rAd population which might be overlooked using other methods. Further, sequencing analysis is performed to exclude occurrence of point mutations, such as introduction of stop codons in the open reading frame of the transgene. More specifically, since viral mutations always present a chance event, one plaque may be stable whereas another one may present a deletion band. Therefore, to correctly assess genetic stability, several viral populations (plaques) need to be tested. In case a mutation occurs, which enables the vector to replicate more efficiently than the parental vector, this can lead to outgrowth of the mutant version, which is often only observed following extended passaging as described in this study. Preferably, the rAd of the present invention are genetically stable for at least up to 10 passages, and even more preferably for at least up to 13 passages in the test system used, such that the virus is sufficiently stable for large scale production campaigns.

The recombinant adenovirus produced according to the methods of the invention can be prepared according to the embodiments described above for the recombinant adenovirus.

The invention also provides a method for expressing at least two transgenes in a cell, the method comprising providing the cell with a recombinant adenovirus according to the invention. Providing a cell with a recombinant adenovirus can be done via administration of the adenovirus to a subject, or via introduction (e.g. infection) of the adenovirus in vitro or ex vivo into a cell. In certain embodiments the invention provides a recombinant adenoviral vector for use in expressing at least two transgenes in a cell, e.g. by administering the recombinant adenovirus to a subject.

The invention also provides a method for inducing an immune response against at least two antigens, comprising administering to a subject a recombinant adenovirus according to the invention. The invention also provides a recombinant adenovirus according to the invention for use in inducing an immune response against at least two antigens.

The invention also provides a recombinant DNA molecule comprising the genome of a recombinant adenovirus of the invention. The skilled person will be aware that this may also be a combination of at least two different recombinant DNA molecules that together can form the single recombinant DNA molecule of the invention. Such molecules are useful in manipulating the genome and creating novel recombinant adenoviruses. The genome encodes the proteins that are required for adenovirus replication and packaging in permissive cells.

The term 'about' for numerical values as used in the present disclosure means the value±10%.

Producer cells are cultured to increase cell and virus numbers and/or virus titers. Culturing a cell is done to enable it to metabolize, and/or grow and/or divide and/or produce virus of interest according to the invention. This can be accomplished by methods such as well-known to persons skilled in the art, and includes but is not limited to providing nutrients for the cell, for instance in the appropriate culture media. Suitable culture media are well known to the skilled person and can generally be obtained from commercial sources in large quantities, or custom-made according to standard protocols. Culturing can be done for instance in dishes, roller bottles or in bioreactors, using batch, fed-batch, continuous systems and the like. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9).

Typically, the adenovirus will be exposed to the appropriate producer cell in a culture, permitting uptake of the virus. Usually, the optimal agitation is between about 50 and 300 rpm, typically about 100-200, e.g. about 150, typical DO is 20-60%, e.g. 40%, the optimal pH is between 6.7 and 7.7, the optimal temperature between 30 and 39° C., e.g. 34-37° C., and the optimal MOI between 5 and 1000, e.g. about 50-300. Typically, adenovirus infects producer cells spontaneously, and bringing the producer cells into contact with rAd particles is sufficient for infection of the cells. Generally, an adenovirus seed stock is added to the culture to initiate infection, and subsequently the adenovirus propagates in the producer cells. This is all routine for the person skilled in the art.

After infection of an adenovirus, the virus replicates inside the cell and is thereby amplified, a process referred to herein as propagation of adenovirus. Adenovirus infection results finally in the lysis of the cells being infected. The lytic characteristics of adenovirus therefore permits two different modes of virus production. The first mode is harvesting virus prior to cell lysis, employing external factors to lyse the cells. The second mode is harvesting virus supernatant after (almost) complete cell lysis by the produced virus (see e.g. U.S. Pat. No. 6,485,958, describing the harvesting of adenovirus without lysis of the host cells by an external factor). It is preferred to employ external factors to actively lyse the cells for harvesting the adenovirus.

Methods that can be used for active cell lysis are known to the person skilled in the art, and have for instance been discussed in WO 98/22588, p. 28-35. Useful methods in this respect are for example, freeze-thaw, solid shear, hypertonic and/or hypotonic lysis, liquid shear, sonication, high pressure extrusion, detergent lysis, combinations of the above, and the like. In one embodiment of the invention, the cells are lysed using at least one detergent. Use of a detergent for lysis has the advantage that it is an easy method, and that it is easily scalable.

Detergents that can be used, and the way they are employed, are generally known to the person skilled in the art. Several examples are for instance discussed in WO 98/22588, p. 29-33. Detergents can include anionic, cationic, zwitterionic, and nonionic detergents. The concentration of the detergent may be varied, for instance within the range of about 0.1%-5% (w/w). In one embodiment, the detergent used is Triton X-100.

Nuclease may be employed to remove contaminating, i.e. mostly from the producer cell, nucleic acids. Exemplary nucleases suitable for use in the present invention include Benzonase®, Pulmozyme®, or any other DNase and/or RNase commonly used within the art. In preferred embodiments, the nuclease is Benzonase®, which rapidly hydrolyzes nucleic acids by hydrolyzing internal phosphodiester bonds between specific nucleotides, thereby reducing the viscosity of the cell lysate. Benzonase® can be commercially obtained from Merck KGaA (code W214950). The concentration in which the nuclease is employed is preferably within the range of 1-100 units/ml. Alternatively, or in addition to nuclease treatment, it is also possible to selectively precipitate host cell DNA away from adenovirus preparations during adenovirus purification, using selective precipitating agents such as domiphen bromide (see e.g. U.S. Pat. No. 7,326,555; (Goerke, To, Lee, Sagar, & Konz, 2005); WO 2011/045378; WO 2011/045381).

Methods for harvesting adenovirus from cultures of producer cells have been extensively described in WO 2005/080556.

In certain embodiments, the harvested adenovirus is further purified. Purification of the adenovirus can be performed in several steps comprising clarification, ultrafiltration, diafiltration or separation with chromatography as described in for instance WO 05/080556, incorporated by reference herein. Clarification may be done by a filtration step, removing cell debris and other impurities from the cell lysate. Ultrafiltration is used to concentrate the virus solution. Diafiltration, or buffer exchange, using ultrafilters is a way for removal and exchange of salts, sugars and the like. The person skilled in the art knows how to find the optimal conditions for each purification step. Also WO 98/22588, incorporated in its entirety by reference herein, describes methods for the production and purification of adenoviral vectors. The methods comprise growing host cells, infecting the host cells with adenovirus, harvesting and lysing the host cells, concentrating the crude lysate, exchanging the buffer of the crude lysate, treating the lysate with nuclease, and further purifying the virus using chromatography.

Preferably, purification employs at least one chromatography step, as for instance discussed in WO 98/22588, p. 61-70. Many processes have been described for the further purification of adenoviruses, wherein chromatography steps are included in the process. The person skilled in the art will be aware of these processes, and can vary the exact way of employing chromatographic steps to optimize the process. It is for instance possible to purify adenoviruses by anion exchange chromatography steps, see for instance WO 2005/080556. Many other adenovirus purification methods have been described and are within the reach of the skilled person. Further methods for producing and purifying adenoviruses are disclosed in for example WO 00/32754, WO 04/020971, U.S. Pat. Nos. 5,837,520, 6,261,823, and WO 2006/108707, all incorporated by reference herein.

For administering to humans, the invention may employ pharmaceutical compositions comprising the rAd and a pharmaceutically acceptable carrier or excipient. In the present context, the term "Pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The purified rAd preferably is formulated and administered as a sterile solution although it is also possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g pH 5.0 to 7.5. The rAd typically is in a solution having a suitable buffer, and the solution of rAd may also contain a salt. Optionally stabilizing agent may be present, such as albumin. In certain embodiments, detergent is added. In certain embodiments, rAd may be formulated into an injectable preparation. These formulations contain effective amounts of rAd, are either sterile liquid solutions, liquid suspensions or lyophilized versions and optionally contain stabilizers or excipients. An adenovirus vaccine can also be aerosolized for intranasal administration (see e.g. WO 2009/117134).

For instance adenovirus may be stored in the buffer that is also used for the Adenovirus World Standard (Hoganson et al., 2002): 20 mM Tris pH 8, 25 mM NaCl, 2.5% glycerol. Another useful formulation buffer suitable for administration to humans is 20 mM Tris, 2 mM $MgCl_2$, 25 mM NaCl, sucrose 10% w/v, polysorbate-80 0.02% w/v. Another formulation buffer that is suitable for recombinant adenovirus comprises 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Obviously, many other buffers can be used, and several examples of suitable formulations for the storage and for pharmaceutical administration of purified (adeno)virus preparations are known, including those that can for instance be found in European patent no. 0853660, U.S. Pat. No. 6,225,289 and in international patent applications WO 99/41416, WO 99/12568, WO 00/29024, WO 01/66137, WO 03/049763, WO 03/078592, WO 03/061708.

In certain embodiments a composition comprising the adenovirus further comprises one or more adjuvants. Adjuvants are known in the art to further increase the immune response to an applied antigenic determinant, and pharmaceutical compositions comprising adenovirus and suitable adjuvants are for instance disclosed in WO 2007/110409, incorporated by reference herein. The terms "adjuvant" and "immune stimulant" are used interchangeably herein, and are defined as one or more substances that cause stimulation of the immune system. In this context, an adjuvant is used to enhance an immune response to the adenovirus vectors of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as E. coli heat labile enterotoxin LT, cholera toxin CT, and the like. It is also possible to use vector-encoded adjuvant, e.g. by using heterologous nucleic acid that encodes a fusion of the oligomerization domain of C4-binding protein (C4 bp) to the antigen of interest (Ogun, Dumon-Seignovert, Marchand, Holder, & Hill, 2008), or heterologous nucleic acid encoding a toll-like receptor (TLR) agonist, such as a TLR3 agonist such as dsRNA (see e.g. WO 2007/100908) or the like. Such rAd according to the invention may for instance encode an antigen of interest on one side of the bidirectional promoter and a TLR3 agonist on the other side of the bidirectional promoter. Such rAd are particularly suited for administration via a mucosal route, e.g. oral administration (see e.g. WO 2007/100908). In certain embodiments the compositions of the invention comprise aluminium as an adjuvant, e.g. in the form of aluminium hydroxide, aluminium phosphate, aluminium potassium phosphate, or combinations thereof, in concentrations of 0.05-5 mg, e.g. from 0.075-1.0 mg, of aluminium content per dose.

In other embodiments, the compositions do not comprise adjuvants.

A pharmaceutical composition according to the invention may in certain embodiments be a vaccine.

Adenovirus compositions may be administered to a subject, e.g. a human subject. The total dose of the adenovirus provided to a subject during one administration can be varied as is known to the skilled practitioner, and is generally between $1 \times 10^7$ viral particles (vp) and $1 \times 10^{12}$ vp, preferably between $1 \times 10^8$ vp and $1 \times 10^{11}$ vp, for instance between $3 \times 10^8$ and $5 \times 10^{10}$ vp, for instance between $10^9$ and $3 \times 10^{19}$ vp.

Administration of adenovirus compositions can be performed using standard routes of administration. Non-limiting embodiments include parenteral administration, such as by injection, e.g. intradermal, intramuscular, etc, or subcutaneous or transcutaneous, or mucosal administration, e.g. intranasal, oral, and the like. In one embodiment a composition is administered by intramuscular injection, e.g. into the deltoid muscle of the arm, or vastus lateralis muscle of the thigh. The skilled person knows the various possibilities to administer a composition, e.g. a vaccine in order to induce an immune response to the antigen(s) in the vaccine.

A subject as used herein preferably is a mammal, for instance a rodent, e.g. a mouse, or a non-human-primate, or a human. Preferably, the subject is a human subject.

It is also possible to provide one or more booster administrations of one or more adenovirus vaccines. If a boosting vaccination is performed, typically, such a boosting vaccination will be administered to the same subject at a moment between one week and one year, preferably between two weeks and four months, after administering the composition to the subject for the first time (which is in such cases referred to as 'priming vaccination'). In alternative boosting regimens, it is also possible to administer different vectors, e.g. one or more adenoviruses of different serotype, or other vectors such as MVA, or DNA, or protein, to the subject as a priming or boosting vaccination.

Various publications, which may include patents, published applications, technical articles and scholarly articles, are cited throughout the specification in parentheses, and full citations of each may be found at the end of the specification. Each of these cited publications is incorporated by reference herein, in its entirety.

Other embodiments, features, and advantages of the invention are further illustrated by reference to the following examples. The examples do not limit the invention in any way. They merely serve to clarify the invention.

EXAMPLES

Without further description, it is believed that one of ordinary skill in the art can, using the preceding description and the following illustrative examples, make and utilize the present invention and practice the claimed methods. The following working examples therefore, specifically point out certain embodiments of the present invention, and are not to be construed as limiting in any way the remainder of the disclosure.

[Comparative] Example 1: Preparation and Characterization of Monovalent Replication Incompetent rAd35 and rAd26 Vectors Generation of E1 Adapter Plasmids Containing Filovirus Glycoproteins Filovirus glycoprotein encoding genes for Marburg virus Angola (MARV) (GenBank® accession number Q1PD50), Ebola virus Zaire strain Mayinga (EBOV) (GenBank® accession number AAN37507.1 with a T544I mutation), and Ebola virus Sudan Gulu (SEBOV) (GenBank® accession number YP_138523 with G2E) were gene-optimized for human expression and cloned into pAdapt35 or pAdapt26 plasmids (Vogels et al. 2007; Abbink et al., 2007), using restriction sites HindIII and XbaI. A Kozak sequence (5' GCCACC 3') was included directly in front of the ATG start codon, and two stop codons (5' TGA TAA 3') were added at the end of the coding sequences. As described herein, the recombinant adenoviruses and vectors are referred to generally as rAd or rAd vectors and more specifically as rAd35 or rAd26.

Cell Culture:

PER.C6 cells (Fallaux et al., 1998) were maintained in Dulbecco's modified Eagle's medium (DMEM) with 10% fetal bovine serum (FBS), supplemented with 10 mM $MgCl_2$.

Adenovirus Generation, Infections and Passaging.

All adenoviruses were generated in PER.C6® cells by homologous recombination and produced as previously described (for rAd35: (Havenga et al., 2006); for rAd26: (Abbink et al., 2007)). Briefly, PER.C6® cells were transfected with rAd vector encoding plasmids, using Lipofectamine according to the instructions provided by the manufacturer (Life Technologies). For rescue of rAd35 vectors carrying the filovirus glycoprotein transgene expression cassette, the pAdApt35 plasmids and pWE/Ad35.pIX-rITR.dE3.5orf6 cosmid were used, whereas for rAd26 vectors, the pAdApt plasmids and pWE.Ad26.dE3.5orf6. cosmid were used. Cells were harvested one day after full cytopathic effect (CPE), freeze-thawed, centrifuged for 5 min at 3,000 rpm, and stored at −20° C. Next the viruses were plaque purified and amplified in PER.C6® cultured on a single well of a multiwell 24 tissue culture plate. Further amplification was carried out in PER.C6® cultured using a T25 tissue culture flask.

Genetic Stability Testing of Adenoviral Vectors in PER.C6® Cells.

Genetic stability testing of the vaccine vectors was performed to ensure genetic stability in the production process, which involves several passages in PER.C6® cells as illustrated in FIG. 1B. Generation, plaque purification, and expansion to T25 format of the recombinant vaccine vectors was achieved as described above. Briefly, recombinant viruses were generated by plasmid transfections in the E1-complementing cell line PER.C6® and plaque-purified. 5 plaques were selected for up-scaling from multiwell 24 (MW24) to a T25 flask (rAd35 p3/rAd26 p4). Subsequently, new PER.C6® cells were infected in T25 format until viral passage number 13 (rAd35 p13/rAd26 p13). The propagation of the viruses was performed using a predetermined infectious volume that would give full cytopathic effect 2 days post infection, which was retrospectively determined to be in a range of virus particle per cell ratio of 50 for rAd35 and 900 for rAd26. Viral DNA was isolated from p13 material and tested for presence of the complete transgene expression cassette by PCR analysis. The vaccine vectors were propagated up to passage number 13 in PER.C6® cells. The propagation was performed in a way to give full CPE two days post infection. rAd35 viruses were harvested 2 days after full CPE, whereas rAd26 viruses were harvested one day after full CPE. Viral DNA was isolated at passage 2, passage 5, passage 10 and passage 13 and absence of deletions was tested by PCR analysis using primers that flank the transgene expression cassette. Absence of deletion mutants was defined by the following parameters: Band size of PCR product corresponds to positive control (PCR product of plasmid used for virus rescue), no additional bands below the expected PCR product (unless additional bands show to be unspecific PCR products because they are also present in the positive control), approved assay: no band in the PCR $H_2O$ control. To further confirm genetic stability the PCR product of the expression cassette plus flanking regions of some plaques were sequenced.

Monovalent rAd.E1 or single-insert vectors using genetic designs as depicted in FIG. 1A are known to be genetically stable in large scale manufacturing, involving several propagation steps for up scaling in a production cell line, such as PER.C6® cells. In order to mimic these propagation steps required for large-scale productions of clinical trial or commercial scale material, adenoviral vectors were generated by transfection in PER.C6® cells and viral clones were isolated by plaque purifications. Five plaques per virus were selected and viral populations were serially passaged in PER.C6® cells seeded in T25 flasks. In contrast to testing only one batch for genetic stability, serially passaging five plaques in parallel up to p13, allows for a more feasible assessment of rAd genome stability. This particular approach to evaluate the genomic stability of a rAd vector is more valuable for a number of reasons. First being the added resolution of looking at several clones of a rAd genome in comparison to evaluating only one rAd clone. The power of the assay is further increased by, serially passaging the several rAd clones up to or even beyond p13, which cannot be compared with merely looking at the genetic stability of 'one' batch. The latter being mainly due to the fact that batches can in some instances be produced at 'low' passage number. Last but not least, analyzing the passaged rAd genomes with a PCR using primers flanking the E1 expression cassette increases the sensitivity of the assay and allows for detection of small deletion mutants in the rAd population, which might be overlooked by restriction enzyme digestion of the viral DNA. rAd35.E1.EBOV, rAd35.E1.SEBOV, rAd35.E1.MARV and rAd26.E1.EBOV were all confirmed to be stable at passage 13 (p13), with no deletion bands as determined by PCR analysis (FIG. 1C). Note that for all 4 viruses, 10 plaques were actually tested but only 5 are shown for each virus in FIG. 1C. The genetic stability results for the monovalent rAd35.E1 and rAd26.E1 vectors were used as a benchmark for genetic stability testing of bivalent adenoviral vectors.

[Comparative] Example 2: Preparation and Characterization of rAd35 and rAd26 Bivalent Vectors Using E1-E3 Strategy As a first example of a published strategy to generate bivalent adenoviral vectors, the E1-E3 strategy was tested as depicted in FIG. 2. FIG. 2A shows the genetic design of the generated viral vectors for both rAd35 and rAd26 vectors, in which one expression cassette is placed in the E1 region and an additional expression cassette is placed in the E3 region. The rAd35 E3 cassettes were created in the inverted orientation as shown in FIG. 2A. Both E1 and E3 cassettes harbor the identical human CMV promoter, but with heterologous polyadenylation signals (Vogels et al., 2007). As a first viral vector, rAd35.E1.EBOV-E3.SEBOV encoding for Filovirus glycoproteins derived from Ebola virus Zaire (EBOV) and Ebola virus Sudan Gulu (SEBOV), was prepared by transfection in PER.C6® cells, plaque purified and five plaques per virus were selected for genetic stability testing at passage 5 (p5), passage 10 (p10), and passage 15 (p15). FIG. 2B shows the results of the identity PCRs performed at p5, p10, and P15. Deletion bands are detected in the E1/E3 identity PCR in 3 out of 5 plaques at p10. At p15 the majority of the virus population of all tested plaques shows partial deletions of the expression cassette in E3. In order to test the effect of the antigens used or of the specific antigen combination, several other E1-E3 bivalent adenoviral vectors were rescued and tested for genetic stability. Table 1 shows that all listed E1-E3 bivalent adenoviral vectors could be rescued, however all tested vectors were genetically unstable based on PCR analysis. In total, six rAd35.E1-E3 modified vectors were successfully rescued, however, all showed genetic instability as tested by E3 identity PCR. In contrast, the two tested rAd26 E1.E3 modified vectors containing either the Filovirus glycoproteins in E1 and E3 or Filovirus glycoprotein and eGFP, were severely impaired in propagation efficiency and therefore difficult to expand. Both vectors showed genetic instability when tested with the identity PCR. This genetic instability was observed for bivalent vectors expressing two Filovirus glycoproteins and for bivalent vectors expressing one Filovirus glycoprotein and eGFP. Thus, the observed genetic instability cannot be attributed to toxicity-induced selection pressure. The conclusion is that the E1-E3-reverse bivalent strategy in rAd26 and rAd35 as denoted in FIG. 2 is not suitable for large-scale production of bivalent adenoviral vectors, despite earlier literature reports suggesting that they are suitable for large-scale production. A possible explanation is that the earlier literature reports were based on limited testing and the genetic stability was not rigorously and systematically analyzed as described here. In particular, it should be noted that PCR analysis after extended passaging using primers flanking the expression cassette, as used in the present studies to measure genetic stability, increases the sensitivity of the assay and allows for detection of small deletion mutants in the rAd population that might be overlooked using other methods such as restriction digests of the rAd genome. The recently reported E1-E3 reverse strategy using heterologous promoters in rAdS describes similar results regarding the rescuability of the vectors (Small et al., 2014). Their results show that inserting expression cassettes with heterologous promoters in the clockwise 5'-3' orientation failed to rescue. The same expression cassette inserted in the counterclockwise 3'-5' orientation however, resulted in vectors that could be rescued in HEK293 cells. The genetic stability of some of the vectors was also shown by restriction enzyme digestion and gel electrophoresis of the viral genome after first and tenth passage on HEK293 cells.

[Comparative] Example 3: Preparation and Characterization of Bivalent rAd35 Vectors with a Bicistronic Expression Cassette in E1

An E1-F2A strategy (depicted in FIG. 3A) was tested as a second strategy to generate bivalent adenoviral vectors. To this end, two genes were cloned in the E1 region downstream of a human CMV promoter, separated by a furin recognition site and the self-cleaving 2A peptide derived from foot-and-mouth-disease virus, resulting in transcription of an mRNA transcript that is being separated by ribosome-skipping (Donnelly et al., 2001; Szymczak et al., 2004). Three different viruses rAd35.E1.eGFP-F2A-Luc, rAd35.E1.Luc-F2A-eGFP and rAd35.E1.MARV-F2A-SEBOV were generated and propagated in PER.C6® up to passage 13. 5 plaques of the three different viruses were propagated in PER.C6 cells and tested by PCR analysis for genetic stability. The viruses were shown to be genetically stable at passage 10 (data not shown), but at passage 13 (p13), 2 of the plaques of rAd35.E1.MARV-F2A-SEBOV showed very faint deletion bands (FIG. 3B). The deletion bands were more clearly seen in highly overexposed agarose gel pictures, confirming that a proportion of these viral populations had partially deleted the bivalent expression cassette by p13. In comparison to the previously tested E1-E3 bivalent strategy, the E1-F2A viral vectors were more genetically stable with no deletion bands up to passage 10 and they could be propagated efficiently.

Therefore, to allow for further evaluation of viruses with the bicistronic E1-F2A design, in particular to evaluate expression levels and immunogenicity of the two transgenes, T25 material of the generated Ad35.E1.MARV-F2A-SEBOV virus was used to inoculate a T175 tissue culture flask. Of the T175 crude lysate, 3 to 5 ml was used to inoculate 20×T175 triple-layer tissue culture flasks containing 70% confluent layers of PER. C6® cells. The virus was then purified using a two-step CsCl purification method and the purified virus was stored in aliquots at 85° C.

Further, viral vectors were generated using a TaV sequence, a 2A sequence derived from Thosea assigna virus and expressing eGFP and luciferase, rAd35.E1.eGFP—TaV-Luc, rAd35.E1.Luc-TaV-eGFP. Expression analysis by Western Blot showed a similar reduction in expression as observed for the F2A constructs. Genetic stability testing also showed comparable results as for F2A constructs. This approach was not further pursued.

For both gene therapy and vaccine applications, potent expression of the encoded transgene is a prerequisite, e.g., for a vaccine to be sufficiently immunogenic there needs to be sufficient expression of the transgenes (antigens) to stimulate T-cell and/or B-cell responses. Since single-insert vaccine vectors as presented in FIG. 1 are highly immunogenic in several animal models and in humans, these single-insert vectors were used as a benchmark for potent expression in an in vitro assay. A549 cells were infected with CsCl purified vaccine vectors at 1000, 2500 and 5000 viral particles per cell (VP/cell). Transgene expression was analyzed by Western Blot using transgene-specific primary antibodies. FIG. 3C shows that the rAd35.E1.MARV-F2A-SEBOV vector drives reduced transgene expression of both encoded transgenes in comparison to the same VP/cell of either rAd35.MARV or rAd35.SEBOV.

Since the filovirus glycoproteins (GPs), MARV and SEBOV, are surface transmembrane proteins, correct post-translational modifications and trafficking are considered important for immunogenicity. Therefore, expression on the cell surface of rAd infected cells was tested in a FACS cell surface expression assay. To this end, A549 cells were infected with bivalent rAd35.E1.MARV-F2A-SEBOV expressing both MARV and SEBOV and with a mixture of the two monovalent vectors rAd35.MARV and rAd35.SEBOV as a benchmark control. Cells were infected with increasing amount of virus (111, 333 and 1000

VP/cell), harvested 48 hours post infection (48 hpi), and GPs on the cell surface were stained using mouse-serum raised against the respective GPs. An anti-mouse APC-coupled secondary antibody was used to facilitate detection of the cells by FACS. % of APC-positive cells was counted. The results presented in FIG. 3D show that correct processing and trafficking of the GPs is maintained, however FACS analysis also confirmed reduced expression of both transgenes for rAd35.E1.MARV-F2A-SEBOV compared to a mixture of rAd35.MARV and rAd35.SEBOV.

To analyze the immune response induced against the encoded transgenes by bivalent rAd35.E1.MARV-F2A-SEBOV, mice were immunized with the purified vaccine vector, using the mix of the two monovalent vectors rAd35.MARV and rAd35.SEBOV as a benchmark control. In this study, animals were distributed in experimental groups of 10 mice. A single dose of $1 \times 10^9$ vector particles (VP) per vector was administered intramuscularly. To compensate for a possible adjuvanting effect in mice injected with 2 single-insert vectors (thus receiving $2 \times 10^9$ VP per animal), animals injected with rAd35.E1.MARV-F2A-SEBOV were also administered $1 \times 10^9$ VP of Ad35.empty vector (thus all mice received $2 \times 10^9$ total VP per animal). The readout for cellular and humoral immune response was an ELISPOT and ELISA at 8 weeks post-immunization.

The ELISPOT assay is used to determine the relative number of GP protein-specific IFNγ-secreting T-cells in the spleen, and is essentially done as described in (Radosevic et al., 2010), with some adaptations. In brief, for stimulation in ELISPOT three different 15-mer peptide pools per Filovirus antigen were used; a consensus pool which contains peptides similar between either the Ebola or Marburg Filovirus glycoproteins, Pool 1 containing the remaining peptides from the N-terminal half of the specific glycoproteins and Pool 2 with peptides containing the remaining peptides from the C-terminal part of the specific Filovirus glycoprotein. The designed overlapping peptides were fully matched to the glycoprotein encoded by the rAd vectors. The numbers of spot-forming units (SFU) per $10^6$ cells were calculated.

For the determination of GP specific antibody titers an SEBOV or MARV glycoprotein specific mouse antibody ELISA was used. ELISA Maxisorp plates (Nunc) were coated overnight (ON) at 4° C. with 10 μg/ml L-PBS, Lectin in PBS (pH 7.4 Gibco). The plates were subsequently blocked for two hours at room temperature (RT) using blocking buffer and coated with in PBS diluted SEBOV and MARV containing HEK293 supernatant. After washing with the wash buffer, the diluted reference standard serum and the test serum were added (in duplicate) to the plates with sample buffer and incubated at RT for one hour. As a negative control naïve mouse serum is taken along. The plates were washed again with wash buffer, coated with anti-mouse IgG-HRP diluted in sample buffer, incubated at RT for 1 hour and developed using OPD (Sigma) solution according to the manufacturers recommendations. After stopping the enzymatic reaction with 1M $H_2SO_4$ the OD was measured at 492 nm using an ELISA plate reader. All the analyses were performed using the GenS software. The serum concentrations in a test sample were reported in ELISA units per milliliter (EU/ml) with the following inclusion and exclusion criteria; the variation of OD between the duplicates in each sample >20% the sample was excluded, the average OD of the naïve serum should be lower than 0.5 and finally per serum sample at least two dilutions should be above OD 0.5 to obtain the correct EU/ml.

FIG. 3E shows the cellular immune response induced by rAd35.E1.MARV-F2A-SEBOV in comparison to the benchmark control, the mix of the respective monovalent vectors. Although a cellular immune response against MARV at 8 weeks post immunization was detected by ELISPOT, no cellular immune response was detected in the SEBOV ELISPOT. FIG. 3F shows the humoral immune response measured by ELISA. The humoral immune response induced by rAd35.E1.MARV-F2A-SEBOV was reduced compared to the one induced by the mix of rAd35.MARV and rAd35.SEBOV.

Figure 3:
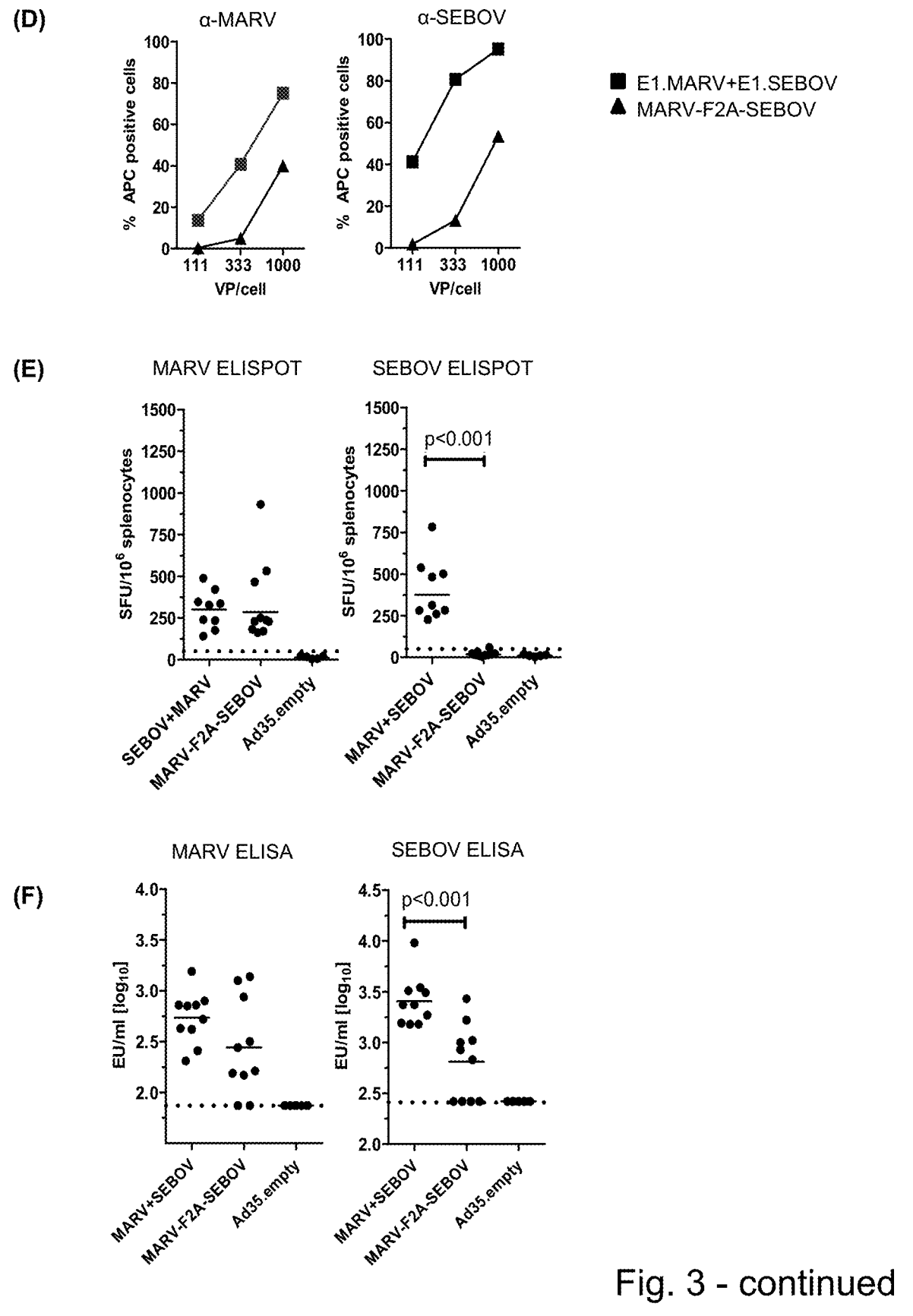

From the experiments presented in FIG. 3 it is evident that rAd35 vectors harboring a bivalent MARV-F2A-SEBOV transgene can be produced and can be genetically stable up to passage 10, but some deletion bands were noted at higher passage numbers (p13) for one of the constructs. Furthermore, transgene expression and immunogenicity induced by the bivalent rAd35.MARV-F2A-SEBOV were both significantly reduced compared to the mix of the monovalent vectors rAd35.MARV and rAd35.SEBOV. Thus, it was determined that the E1-F2A strategy for bivalency is inferior to the mix of the monovalent vectors and it is not optimal for use in gene therapy or vaccine applications.

[Comparative] Example 4: Preparation and Characterization of rAd35 Bivalent Vectors with Two Expression Cassettes in a Head-to-Tail Configuration in E1

Figure 4:
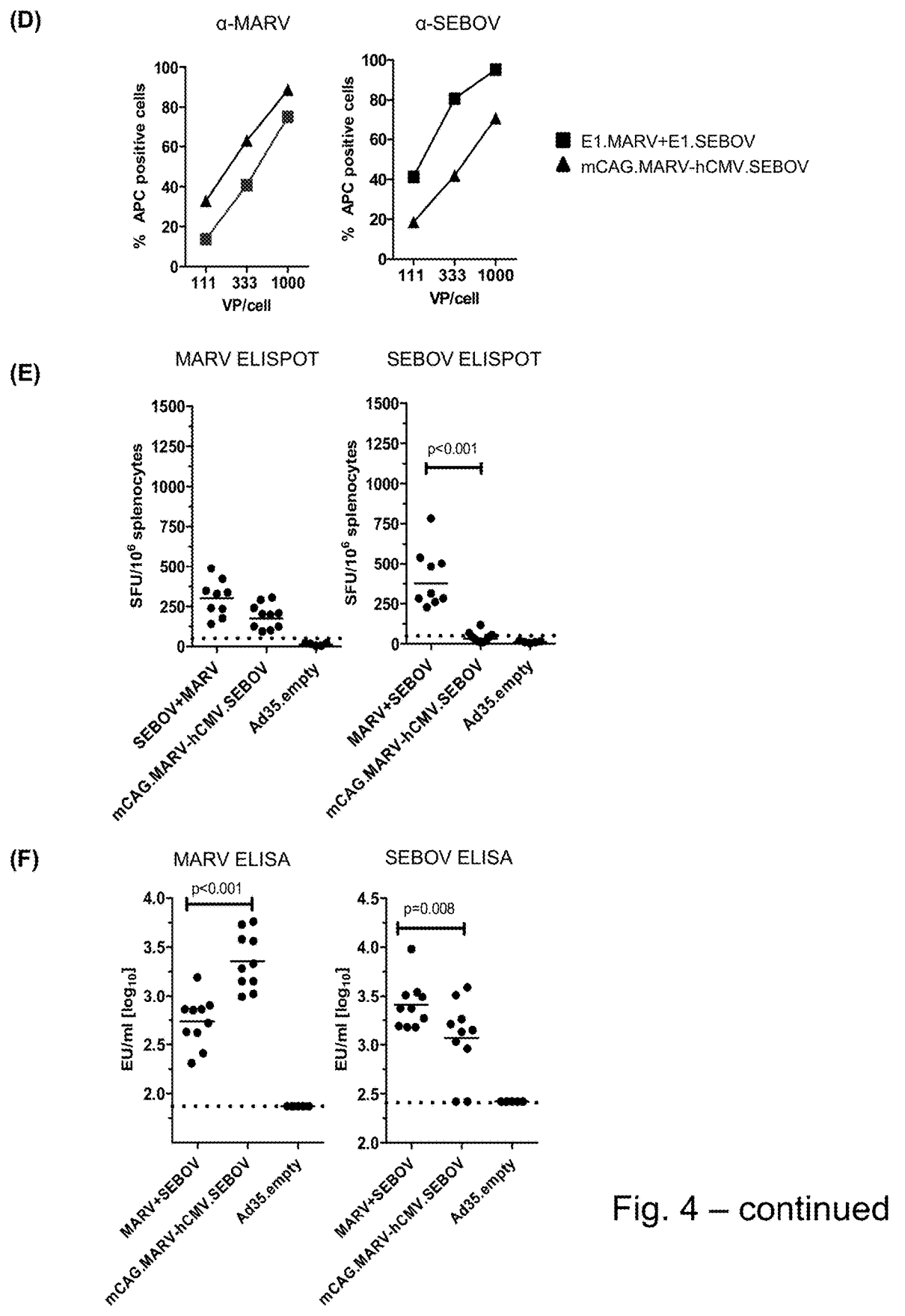

As a third strategy to generate bivalent rAd vectors it was tested whether two expression cassettes could be inserted in a head-to-tail configuration in the E1 region. A schematic representation of the design is shown in FIG. 4A. Two genes are cloned in the E1 region driven by heterologous promoters mCAG (gene 1) and hCMV (gene 2). Different vectors namely rAd35.mCAG.Luc-hCMV.eGFP and rAd35.mCAG.MARV-hCMV.SEBOV were generated and tested for genetic stability of the expression cassette by propagation in PER.C6® up to passage 13. Five plaques were tested for each vector. One plaque of rAd35.mCAG.Luc-hCMV.eGFP was found unstable as indicated by the PCR band in FIG. 4B (lane 2). In contrast, the rAd35.mCAG.MARV-hCMV.SEBOV showed no such deletion bands in neither of the tested plaques.

Transgene expression from the rAd with head-to-tail transgene configuration in E1 driven by the heterologous promoters was tested by Western Blot and the expression was compared to the above described benchmark single insert vectors as indicated in FIG. 4C. A549 cells were transduced with 1000, 2500 and 5000 (VP/cell) and the transgene production was analyzed by Western Blot using antigen specific primary antibodies. There were comparable levels of MARV transgene expression from the bivalent rAd when compared to the benchmark monovalent vectors, but slightly reduced levels of SEBOV expression were observed.

As an additional control of correct processing and presentation of the glycoprotein transgenes, surface staining by FACS (% of positive cells) of vector rAd35.mCAG.MARV-hCMV.SEBOV transduced A549 cells (111, 333 and 1000 VP/cell) was performed with the respective antigen specific antibodies. The direct comparison with the single insert benchmark controls, rAd35.SEBOV and rAd35.MARV, shows higher levels of surface associated MARV and lower levels of surface associated SEBOV were produced by the rAd35.mCAG.MARV-hCMV.SEBOV vector (FIG. 4D).

rAd35.mCAG.MARV-hCMV.SEBOV was further tested for immunogenicity in mice. 10 mice per group, were intramuscularly immunized with a single dose ($1 \times 10^9$) of purified vaccine vector and directly compared to a mix of the two monovalent vectors rAd35.MARV and rAd35.SEBOV. Humoral and cellular immune responses were analyzed by ELISPOT and ELISA 8 weeks post immunization (FIG. 4E-F). The detected MARV antibody titers were higher for rAd35.mCAG.MARV-hCMV.SEBOV immunized mice than in the control animals. By contrast the SEBOV specific antibody levels were reduced in rAd35.mCAG.MARV-hCMV.SEBOV immunized mice as compared to the control animals. Further, T-cell responses against both MARV and SEBOV antigens induced by rAd35.mCAG.MARV-hCMV.SEBOV were reduced compared to the control animals immunized with the mix of the respective monovalent vectors. Thus it was determined that the bivalent head-to-tail configuration in E1 driven by heterologous promoters is inferior to the mix of the monovalent vectors, and this bivalent head-to-tail configuration is thus not optimal for use in gene therapy or vaccine applications.

Figure 5:
FIG. 5: Design and testing of bivalent E1 rAd35 vectors expressing eGFP and Firefly Luciferase (Luc) with three different bidirectional promoters, $P_{bidir1}$, $P_{bidir2}$, and $P_{bidir3}$. (A) Schematic design of the bidirectional expression cassette in E1: The E1 region contains an expression cassette driven by one of the bidirectional promoters, $P_{bidir1}$, $P_{bidir2}$, or $P_{bidir3}$. In the expression cassette, gene 1 is placed on the 5' side in the inverted orientation and gene 2 on the 3' side in the forward orientation. (B) Shown are bar graphs of the Luciferase and eGFP expression levels in HEK293 cells that were transient transfected with E1 rAdApt35 vectors with the three different bidirectional promoter variants that include Luc and eGFP swapped in the gene 1 and gene 2 positions. Also included as controls are the expression levels of Luciferase and eGFP from monovalent vectors when used individually (pAdApt35.eGFP or AdApt35.Luc) or in combination (pAdApt35.eGFP+AdApt35.Luc). The expression level of eGFP is shown as mean fluorescent intensity (MFI) and the expression level of Luciferase is shown as relative light units (RLU). (C) Shown are bar graphs of the expression levels of Luciferase or eGFP in A549 cells infected with E1 rAd35 vectors with the selected $P_{bidir3}$ bidirectional promoter with Luc and eGFP and swapped in the gene 1 and gene 2 positions. Also included as controls are the expression levels of Luciferase and eGFP from an empty rAd35 vector with no transgene (rAd35.empty) and monovalent vectors used individually (rAd35.eGFP or rAd35.Luc). A549 cells were infected with 1000 VP/cell and expression was determined at 48 hpi. The expression level of eGFP is shown as mean fluorescent intensity (MFI) and the expression level of Luciferase is shown as relative light units (RLU). (D) A schematic representation of the $P_{bidir3}$ bidirectional promoter with mCMV IE1/IE2 flanked by two introns, Intron 2 on the 5' side and Intron 1 on the 3' side.
Figure 5:
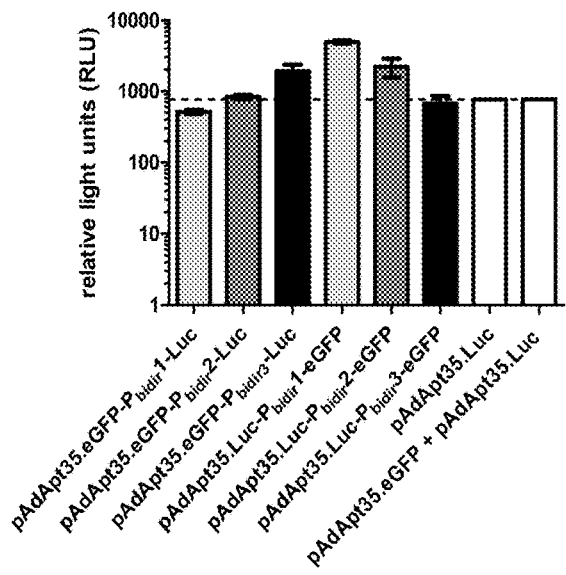
Figure 5:
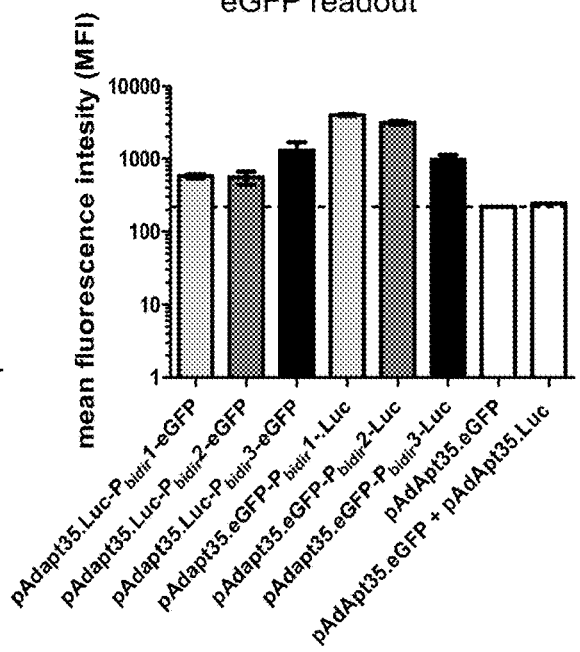

Example 5: Preparation and Characterization of Adenoviral Vectors Harboring a Mouse CMV IE1/IE2 Bidirectional Promoter Finally, the fourth option to generate multivalent rAd was designed where two genes of choice can be inserted in the E1 region. In contrast to the previously discussed designs, the antigens are driven by a bidirectional promoter ($P_{bidir}$ or bidir) and placed in an inverted orientation on the 5' side of the promoter and in the right orientation on the 3' side. Since the objective was to find a bidirectional promoter expressing similar levels of both encoded transgenes, denoted here as a balanced transgene expression, several different bidirectional promoter designs were tested for potency and balance of transgene expression (FIG. 5). First three different bidirectional promoters denoted bidir1-3 were tested for potency and balance by transient transfection of the pAdapt35 plasmids in HEK293 cells and analysis of luciferase (Luc) and eGFP expression levels. The designs of P bidir1, P bidir2 and P bidir3 were unrelated and generated to identify a potent bidirectional promoter. While P bidir 3 is based on the naturally occurring bidirectional mouse CMV promoter, P bidir 1 and P bidir 2 are synthetic bidirectional promoter designs using ubiquitously strong promoters as known in the art in a head-to-head configuration with only one enhancer sequence present (Amendola et al., Nature Biotechnology 2005). The reporter genes eGFP and Luc were placed on either the 5' or 3' side of the promoter (as shown in FIG. 5A) and compared for the respective reporter gene expression. The relative eGFP mean fluorescence intensity (MFI) and Luciferase relative light units (RLU) recorded for each promoter and reporter gene combination were measured in HEK293 cells (transient transfection) and A549 cells (virus infection). Luciferase activity was measured in cell lysates in presence with 0.1% DTT (1M), in Luminoskan™ Ascent Microplate Luminometer. The eGFP fluorescence was measured in the flow cytometer (FACS) by, trypsinizing, centrifuging, and re-suspending cell pellets in PBS/1% FBS (non-virus material) or in CellFix (virus material).

Transient reporter gene expression in HEK293 cells, illustrate the bidir3 promoter to be the most potent and balanced promoter. When directly compared to the bidir1 and bidir2 promoters the most balanced expression of Luc and eGFP was found for the bidir3 promoter. In regard to potency, both bidir1 and bidir2 promoters were outperformed by the reporter genes expression levels recorded for the bidir3 promoter (FIG. 5B).

To confirm the results obtained with the transient transfections in HEK293 cells, rAd35.eGFP-bidir3-Luc and rAd35.Luc-bidir3-eGFP adenoviral vectors were generated and the expression of the reporter genes was tested in A549 cells infected with 1000 VP/cell (FIG. 5C). Direct reporter eGFP and firefly luciferase expression comparison between the bidir3 double insert vectors to the respective single insert controls, shows comparable levels of eGFP regardless of the position in respect to the promoter. The luciferase expression on the other hand is higher when the luciferase gene is positioned at the 3' side compared to the 5' side of the promoter. Nevertheless, reporter gene expression levels recorded for the bidir3 double insert vectors exceed the levels recorded for the single insert vector controls, indicating bidir3 as the more potent promoter (FIG. 5C).

Thus it was determined that an rAd with a bidirectional mouse CMV promoter is superior to previously reported bivalent rAd with regard to levels of expression of the two transgenes, eGFP and Luc. Furthermore, expression of the two transgenes from rAd with a bidir3 bidirectional promoter was also better than the benchmark monovalent vectors that were tested. Therefore, it was determined that the rAd with a bidir3 bidirectional promoter would be suitable for use in gene therapy or vaccine applications with regard to levels of expression of the transgenes.

Figure 6:
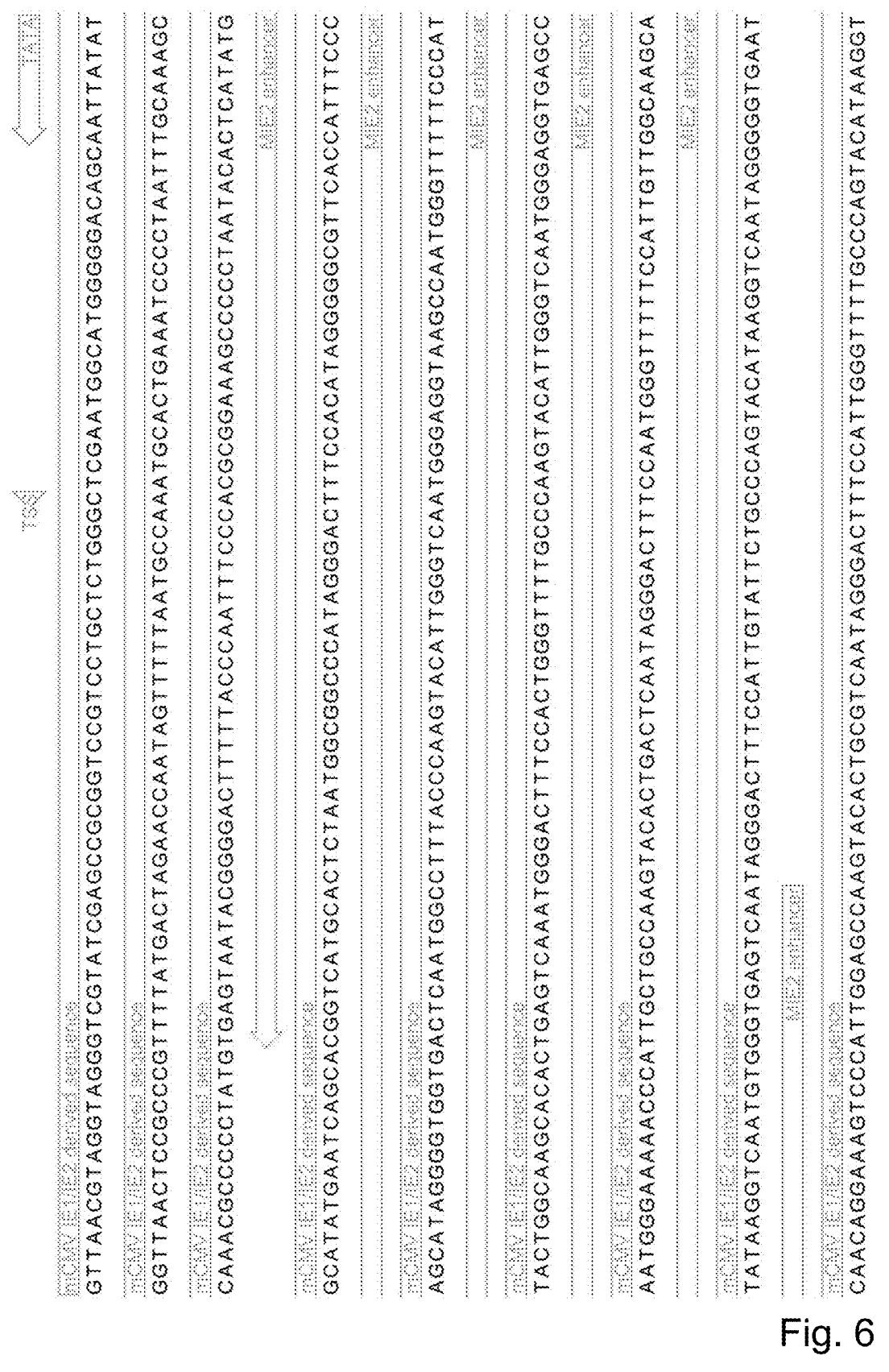
Figure 6:
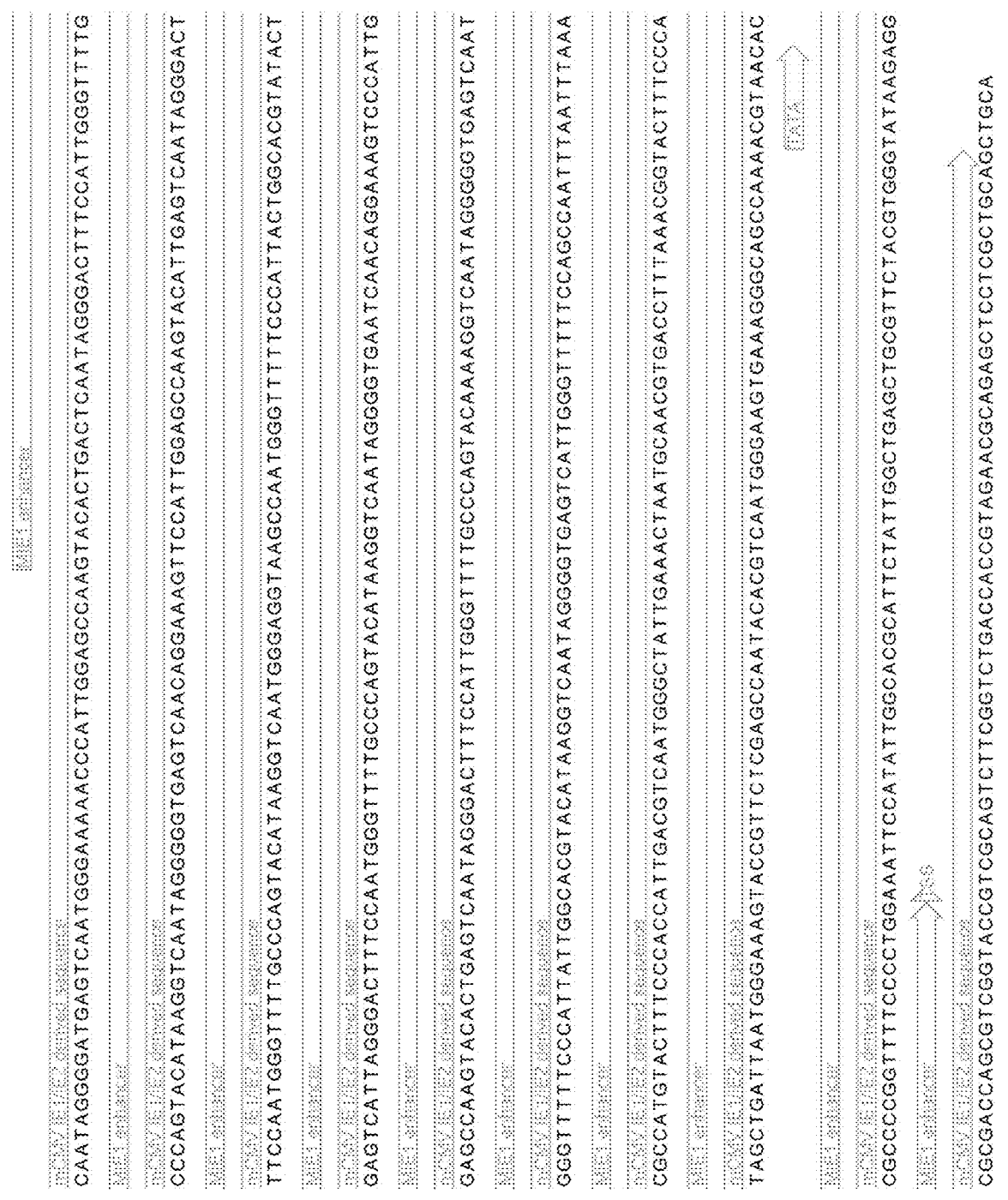

A representative design of an mCMV IE1/IE2 promoter is shown in FIG. 6 with the sequence and the corresponding annotations indicated with stacked arrows. The mCMV IE1/IE2 core sequence contains two MIE1 and MIE2 enhancer sequences driving the expression in both directions. In addition, the sequence contains two TATA boxes and two transcriptional start sites (TSS) both flanked by respective human ApoE1 and chimeric intron sequences (see FIGS. 5D and 6). A representative sequence for a mCMV bidirectional promoter sequence including introns (bidir3) is provided as SEQ ID NO:1 and a representative sequence for a mCMV bidirectional promoter sequence excluding introns is provided as SEQ ID NO:2.

Example 6: Preparation and Characterization of rAd35 Bivalent Vectors with a mCMV Bidirectional Expression Cassette A selected mCMV bidirectional promoter is schematically represented in FIG. 7A, depicting the orientation of the inserted genes and position in rAd35 vector genome. Different rAd35 vectors were tested for genetic stability up to p13 in PER.C6® cells, expression levels of antigens (total and surface expression) and immunogenicity in mice (FIG. 7).

The different rAd vectors were also evaluated for rescueability in PER.C6® cells and genetic stability at p13. The data are summarized in Table 2. The genetic stability was assessed for each vector by passaging the five plaques in PER.C6® up to p13. All vectors were found to be genetically stable at p13, with no deletion bands (FIG. 7B). The data in FIG. 7B is a representative set for three vectors, rAd35.eGFP-mCMV-Luc, rAd35.Luc-mCMV-eGFP and rAd35.MARV-mCMV-SEBOV where viral DNA was isolated at passage 13 (p13) and PCR was performed using primers flanking the E1 expression cassette.

Subsequently the expression levels of rAd35.MARV-mCMV-SEBOV were evaluated for both total expression (Western Blot, FIG. 7C) and surface expression (FACS, FIG. 7D) using anti-MARV and anti-SEBOV antibodies. To assess the total expression levels of SEBOV and MARV, A549 were infected with 1000, 2500 and 5000 VP/cell and directly compared with the single insert vectors, rAd35.E1MARV or rAd35.SEBOV. No obvious difference in total protein levels of MARV was observed between the rAd35.MARV-mCMV-SEBOV and rAd35.E1.MARV. On the contrary, the protein levels detected for SEBOV expressed from rAd35.MARV-mCMV-SEBOV exceeded the single insert control rAd35.E1.SEBOV (FIG. 7C). The antigen MARV and SEBOV expression on the cellular surface was tested by infecting A549 cells with 111, 333 and 1000 VP/cell rAd35.MARV-mCMV-SEBOV or a mixture of rAd35.E1MARV+rAd35.E1SEBOV and analyzing the MARV or SEBOV positive cells (%) in FACS 48 hours post infection (48 hpi). Compared to the control mixture of monovalent vectors, both the anti-MARV staining and the anti-SEBOV staining in FACS showed higher percentages of positive cells with rAd35.MARV-mCMV-SEBOV (FIG. 7D).

Next, the immunogenicity of rAd35.MARV-mCMV-SEBOV ($2\times10^9$ VP) was directly compared to a mixture of the respective single insert controls, rAd35.E1.MARV+rAd35.E1.SEBOV ($2\times10^9$ VP), by looking at the induced MARV and SEBOV specific T-cell responses and B-cell responses (FIGS. 7E and F, respectively). The ELISPOT results in FIG. 7E represent the MARV and SEBOV positive T-cell fractions in spot forming units per $10^6$ (SFU/$10^6$) in mice splenocytes, eight weeks post immunization. The SEBOV induced T-cell response was higher in the group of mice immunized with rAd35.MARV-mCMV-SEBOV than with the mixture of single insert vectors, rAd35.MARV+rAd35.SEBOV (FIG. 7E). The MARV induced T-cell response in the group of mice immunized with the double insert Ad35.MARVA-mCMV-SEBOV was non-inferior to the rAd35.MARV+rAd35.SEBOV mixture (FIG. 7E). The corresponding SEBOV and MARV specific B-cell responses were measured in ELISA and expressed as ELISA units per ml (EU/ml). Both MARV and SEBOV specific B-cell responses were higher in the group of mice immunized with the double insert rAd35.MARV-mCMV-SEBOV as compared to the single insert mixture of rAd35.MARV+rAd35.SEBOV (FIG. 7F).

Thus, according to the results presented above for rAd35.MARV-mCMV-SEBOV, it was determined that an rAd35 with a bidirectional mouse CMV promoter expressing MARV and SEBOV is superior to previously reported bivalent rAd with regard to genetic stability, levels of expression of the two transgenes, and immunogenicity. Furthermore, it was determined that rAd35 with a bidirectional mouse CMV promoter provide sufficient expression levels of both transgenes to generate significant T-cell and B-cell immune responses to both antigens. Therefore, it was determined that the rAd35 with a bidirectional mouse CMV promoter would be suitable for use in gene therapy and vaccine applications with regard to genetic stability, levels of expression of the transgenes, and immunogenicity of the expressed antigens.

Example 7: Preparation and Characterization of rAd26 Bivalent Vectors Using a mCMV Bidirectional Expression Cassette The bivalent bidirectional promoter expression cassette containing MARV and SEBOV antigens (MARV.mCMV.SEBOV) was extensively tested in rAd26 for genetic stability, expression levels of the two antigens (total and surface), and immunogenicity in mice against the encoded antigens. The overall design of rAd26 follows the rAd35 design where the expression cassette is places in the E1 region and each antigen is controlled by the centrally placed bidirectional mCMV promoter (FIG. 8A). For genetic stability testing, rAd26.MARV.mCMV.SEBOV was passaged up to 13 passages (p13) in PER.C6®. Viral DNA was isolated at p13 and analyzed by PCR for potential deletions in E1 by using primers flanking the bidirectional transgene expression cassette (FIG. 8B). No deletion bands were detected in the tested plaques, indicating a good genetic stability profile of rAd26.MARV.mCMV.SEBOV. In addition, the PCR products of the p13 plaques were sequenced and the sequencing confirmed the absence of mutations and stop codons. Thus, based on PCR analysis and sequencing, rAd26.E1.MARV-mCMV-SEBOV is genetically stable.

The total protein expression levels of the MARV and SEBOV antigens encoded in the rAd26.E1.MARV.mCMV.SEBOV were assessed by infecting A549 cells with 10000, 25000 and 50000 VP/cell, lysing the cells 48 hpi, and staining with anti-MARV or anti-SEBOV antibodies in a Western Blot (FIG. 8C). The protein expression from the double insert vector was directly compared to the single insert vectors, rAd26.E1.SEBOV and rAd26.E1.MARV. Staining with anti-MARV showed a reduced MARV expression in the cells infected with the double insert vector rAd26.E1.MARV.mCMV.SEBOV when compared to the rAd26.E1.MARV. On the other hand, increased amounts of SEBOV were detected in the cells infected with rAd26.E1.MARV.mCMV.SEBOV when compared to the single insert control rAd26.E1.MARV (FIG. 8C).

Surface expression of the MARV and SEBOV antigens was assessed by infecting A549 cells with 100000, 20000, 4000 and 800 VP/cell, staining with anti-MARV or anti-SEBOV 48 hours after infection (48 hpi) and analyzing the MARV or SEBOV percent (%) positive cells by FACS (FIG. 4D). The difference in the MARV expression observed in A549 lysates was not detected in the FACS analysis of rAd26.E1.MARV.mCMV.SEBOV infected A549 cells. Here, in contrast to what was found with the Western Blot for total protein expression, equal amounts of MARV were detected on the surface of the cells infected with the rAd26.E1.MARV.mCMV.SEBOV and rAd26.E1.MARV (FIG. 8D). Furthermore, there was no difference observed between the amounts of surface expressed SEBOV in cells infected with rAd26.E1.MARV.mCMV.SEBOV and rAd26.E1.SEBOV. The FACS result for SEBOV expression on the cell surface was consistent with the total protein staining in Western Blot (FIGS. 8C and D).

The immunogenic potency of rAd26.E1.MARV.mCMV.SEBOV was evaluated by comparing the ability of the bivalent vector and a mixture of the single insert vectors to induce MARV and SEBOV specific T-cell and B-cell responses with ELISPOT and ELISA assays, respectively. For both assays, 12 mice per group were immunized intramuscularly (IM) with $1\times10^9$ VP of rAd26.E1.MARV-mCMV-SEBOV or with a mixture of $1\times10^9$ VP rAd26.E1.MARV and $1\times10^9$ VP rAd26.E1.SEBOV. To account for the possible adjuvating effect of the group receiving the total of $2\times10^9$ VP of single insert combination, $1\times10^9$ VP rAd26.empty vector was co-injected with the rAd26.E1.MARV-mCMV-SEBOV. As a negative control, two groups of five mice received a total of $2\times10^9$ VP rAd26.emtpy. Prior to vaccination, mice were also bled to generate naïve control serum (data not shown). The ELISPOT and ELISA assay results are shown as FIGS. 8E and F, respectively.

The MARV and SEBOV specific T-cell responses, as measured in spot forming units/$10^6$ splenocytes (SFU/$10^6$)

by ELISPOT, showed some differences between the double insert vector and the mixture of the single insert vectors, but the differences were only significant at the lower doses of $2 \times 10^9$ VP. In the group of mice immunized with the lower dose of the mixture, $2 \times 10^9$ VP rAd26.E1.SEBOV+ rAd26.E1.MAR, there were significantly higher ($p<0.01$) MARV and ($p<0.05$) SEBOV specific T-cell responses as compared to the same dose of rAd26.E1.MARV.mCMV.SEBOV. These differences, however, were not observed for MARV or SEBOV specific T-cell responses in mice immunized with the higher $2 \times 10^{10}$ VP dose of the vectors. Furthermore, the double insert vector provided potent T-cell responses for both antigens (FIG. 8E).

Based on the ELISA data there were also some differences in the B-cell response for the double insert vector compared to the mixture of the single insert vectors, but the differences were only seen with MARV. For SEBOV, there were no significant differences in the levels of SEBOV antibodies in mice immunized with either dose of the different vectors (FIG. 8F). For the MARV specific B-cell responses, there were significantly higher ($p<0.01$) IgG levels (ELISA units per ml (EU/ml)), for the mice immunized with either dose of the mixture containing the single inserts rAd26.E1.SEBOV+ rAd26.E1.MARV compared to the same doses for the double insert rAd26.E1.MARV.mCMV.SEBOV (FIG. 8F). Here again, however, the ELISA showed that the double insert vector provided potent B-cell responses.

Thus, according to the data from FACS analysis for surface expression of the transgenes and the ELISPOT and ELISA assays to measure immunogenicity, the double insert vector rAd26.E1.MARV.mCMV.SEBOV was determined to provide potent expression and potent T-cell and B-cell immune responses against both the MARV and SEBOV antigens. There were some differences detected for the antigens with the double insert vector compared to the mixture of the single insert vectors, but rAd26.E1.MARV.mCMV.SEBOV provided high levels of surface expression of the two transgenes and induced potent T-cell and B-cell responses. Furthermore, based on PCR analysis and sequencing, rAd26.E1.MARV-mCMV-SEBOV was genetically stable. Therefore, it was determined that like rAd35 with a bidirectional mouse CMV promoter, rAd26 with a bidirectional mouse CMV promoter would be suitable for use in gene therapy and vaccine applications with regard to genetic stability, transgene expression, and immunogenicity of the expressed antigens.

CONCLUSION

As described supra, a large number of mCMV bidirectional promoter vectors, rAd35 and rAd26 containing different Filovirus glycoproteins as well as reporter genes (eGFP and Luciferase), were tested for genetic stability in PER.C6® cells, transgene protein expression (total and surface), and immunogenicity of the antigens with regard to both T-cell and B-cell responses. Considering the number of vectors tested, with five or more plaques tested for each vector, and the sensitivity of the E1 expression cassette PCR analysis for genetic stability, the rAd of the present invention with a bidirectional mCMV promoter were determined to be genetically stable with no deletion bands at p13. Furthermore, based on FACS analysis of transgene expression and ELISPOT and ELISA analysis of the immunogenicity of the expressed antigens with regard to T-cell and B-cell responses, the rAd of the present invention with a bidirectional promoter were determined to be suitable for use in gene therapy and vaccine applications. Thus, the rAd of the present invention with a mCMV bidirectional promoter provide a significant improvement compared to the bivalent rAd vectors previously described in the art.

TABLE 1

Rescue attempt, rescue result, and genome stability for rAd35 and rAd26 vectors using the E1-E3 design described in FIG. 2A. The results indicate that bivalent rAds with one antigen encoded in E1 and one in E3 are genetically unstable and difficult to expand.

| Vector and Transgenes | Rescue Attempt | Rescue Result | Genome Stability |
|---|---|---|---|
| rAd35 | | | |
| E1.EBOV-E3.SEBOV | 1 | successful | unstable |
| E1.SEBOV-E3.EBOV | 1 | successful | unstable |
| E1.MARV-E3.EBOV | 1 | successful | unstable |
| E1.MARV-E3.SEBOV | 1 | successful | unstable |
| E1.eGFP-E3.EBOV | 1 | successful | unstable |
| E1.eGFP-E3.SEBOV | 1 | successful | unstable |
| rAd26 | | | |
| E1.EBOV-E3.SEBOV | 2 | difficult to expand | unstable |
| E1.eGFP-E3.SEBOV | 2 | difficult to expand | unstable |

TABLE 2

Rescue attempt, rescue result, and genome stability for rAd vectors harbouring a mCMV bidirectional expression cassette with different transgenes.

| Vector and Transgenes | Rescue Attempt | Rescue Result | Genome Stability |
|---|---|---|---|
| rAd35 | | | |
| Luc-mCMV-eGFP | 1 | successful | stable |
| eGFP-mCMV-Luc | 1 | successful | stable |
| MARV-mCMV-SEBOV | 1 | successful | stable |
| SEBOV-mCMV-MARV | 1 | successful | stable |
| MARV-mCMV-CIEBOV | 1 | successful | stable |
| CIEBOV-mCMV-MARV | 1 | successful | stable |
| EBOV-mCMV-SEBOV | 1 | successful | stable |
| SEBOV-mCMV-EBOV | 1 | successful | stable |
| rAd26 | | | |
| Luc-mCMV-eGFP | 1 | successful | stable |
| MARV-mCMV-SEBOV | 1 | successful | stable |
| EBOV-mCMV-SEBOV | 1 | successful | stable |
| SEBOV-mCMV-EBOV | 1 | not successful | — |
| MARV-mCMV-CIEBOV | 1 | successful | stable |
| CIEBOV-mCMV-MARV | 1 | successful | stable |

REFERENCES

U.S. Patent Documents

U.S. Pat. No. 5,057,540A (Oct. 15, 1991). "Saponin adjuvant". Kensil, Charlotte A.; Marciani, Dante J.
U.S. Pat. No. 5,122,458A (Jun. 16, 1992). "Use of a bGH gDNA polyadenylation signal in expression of non-bGH polypeptides in higher eukaryotic cells". Post, Leonard E.; Palermo, Daniel P.; Thomsen, Darrell R.; Rottman, Fritz M.; Goodwin, Edward C.; Woychik, Richard P.
U.S. Pat. No. 5,559,099A (Sep. 24, 1996). "Penton base protein and methods of using same". Wickham, Thomas J.; Kovesdi, Imre; Brough, Douglas E.; McVey, Duncan L.; Brader, Joseph T.
U.S. Pat. No. 5,837,511A (Nov. 17, 1998). "Non-group C adenoviral vectors". Falck Pedersen, Erik S.; Crystal, Ronald G.; Mastrangeli, Andrea; Abrahamson, Karil U.S. Pat. No. 5,837,520A (Nov. 17, 1998). "Method of purification of viral vectors". Shabram, Paul W.; Huyghe, Bernard G.; Liu, Xiaodong; Shepard, H. Michael U.S. Pat. No. 5,846,782A (Dec. 8, 1998). "Targeting adenovirus with use of constrained peptide motifs". Wickham, Thomas J.; Roelvink, Petrus W.; Kovesdi, Imre U.S. Pat. No. 5,851,806A (Dec. 22, 1998). "Complementary adenoviral systems and cell lines". Kovesdi, Imre; Brough, Douglas E.; McVey, Duncan L.; Bruder, Joseph T.; Lizonova, Alena U.S. Pat. No. 5,891,690A (Apr. 6, 1999). "Adenovirus E1-complementing cell lines". Massie, Bernard U.S. Pat. No. 5,965,541A (Oct. 12, 1999). "Vectors and methods for gene transfer to cells". Wickham, Thomas J.; Kovesdi, Imre; Brough, Douglas E.

U.S. Pat. No. 5,981,225A (Nov. 9, 1999). "Gene transfer vector, recombinant adenovirus particles containing the same, method for producing the same and method of use of the same". Kochanek, Stefan; Schiedner, Gudrun U.S. Pat. No. 5,994,106A (Nov. 30, 1999). "Stocks of recombinant, replication-deficient adenovirus free of replication-competent adenovirus". Kovesdi, Imre; Brough, Douglas E.; McVey, Duncan L.; Bruder, Joseph T.; Lizonova, Alena U.S. Pat. No. 5,994,128A (Nov. 30, 1999). "Packaging systems for human recombinant adenovirus to be used in gene therapy". Fallaux, Frits Jacobus; Hoeben, Robert Cornelis; Van der Eb, Alex Jan; Bout, Abraham; Valerio, Domenico U.S. Pat. No. 6,020,191A (Feb. 1, 2000). "Adenoviral vectors capable of facilitating increased persistence of transgene expression". Scaria, Abraham; Gregory, Richard J.; Wadsworth, Samuel C.

U.S. Pat. No. 6,040,174A (Mar. 21, 2000). "Defective adenoviruses and corresponding complementation lines". Imler, Jean Luc; Mehtali, Majid; Pavirani, Andrea U.S. Pat. No. 6,083,716A (Jul. 4, 2000). "Chimpanzee adenovirus vectors". Wilson, James M.; Farina, Steven F.; Fisher, Krishna J.

U.S. Pat. No. 6,113,913A (Sep. 5, 2000). "Recombinant adenovirus". Brough, Douglas E.; Kovesdi, Imre U.S. Pat. No. 6,225,289B1 (May 1, 2001). "Methods and compositions for preserving adenoviral vectors". Kovesdi, Imre; Ransom, Stephen C.

U.S. Pat. No. 6,261,823B1 (Jul. 17, 2001). "Methods for purifying viruses". Tang, John Chu Tay; Vellekamp, Gary; Bondoc, Jr., Laureano L.

U.S. Pat. No. 6,485,958B2 (Nov. 26, 2002). "Method for producing recombinant adenovirus". Blanche, Francis; Guillaume, Jean Marc U.S. Pat. No. 7,326,555B2 (Feb. 5, 2008). "Methods of adenovirus purification". Konz, Jr., John O.; Lee, Ann L.; To, Chi Shung Brian; Goerke, Aaron R U.S. Pat. No. 8,932,607B2 (Jan. 13, 2015). "Batches of recombinant adenovirus with altered terminal ends". Custers, Jerome H. H. V.; Vellinga, Jort European Patent Documents EP1230354B1 (Jan. 7, 2004). "PERMANENT AMNIOCYTE CELL LINE, THE PRODUCTION THEREOF AND ITS USE FOR PRODUCING GENE TRANSFER VECTORS". KOCHANEK, Stefan; SCHIEDNER, Gudrun EP1601776B1 (Jul. 2, 2008). "EXPRESSION VECTORS COMPRISING THE MCMV IE2 PROMOTER". CHATELLARD, Philippe; IMHOF, Markus EP853660B1 (Jan. 22, 2003). "METHOD FOR PRESERVING INFECTIOUS RECOMBINANT VIRUSES, AQUEOUS VIRAL SUSPENSION AND USE AS MEDICINE". SENE, Claude International Patent Documents WO2003049763A1 (Jun. 19, 2003). "COMPOSITION FOR THE PRESERVATION OF VIRUSES COMPOSITION POUR LA CONSERVATION DE VIRUS". SETIAWAN, Kerrie; CAMERON, Fiona, Helen WO2003061708A1 (Jul. 31, 2003). "STABILIZED FORMULATIONS OF ADENOVIRUS". PUNGOR, Erno WO2003078592A2 (Sep. 25, 2003). "METHOD FOR THE PURIFICATION, PRODUCTION AND FORMULATION OF ONCOLYTIC ADENOVIRUSES". MEMARZADEH, Bahram; PENNATHUR-DAS, Rukmini; WYPYCH, Joseph; YU, De Chao WO2003104467A1 (Dec. 18, 2003). "MEANS AND METHODS FOR THE PRODUCTION OF ADENOVIRUS VECTORS". VOGELS, Ronald; BOUT, Abraham WO2004001032A2 (Dec. 31, 2003). "STABLE ADENOVIRAL VECTORS AND METHODS FOR PROPAGATION THEREOF". VOGELS, Ronald; HAVENGA, Menzo, Jans, Emco; ZUIJDGEEST, David, Adrianus, Theodorus WO2004004762A1 (Jan. 15, 2004). "ISCOM PREPARATION AND USE THEREOF". MOREIN, Bror; LOVGREN BENGTSSON, Karin WO2004020971A2 (Mar. 11, 2004). "CHROMATOGRAPHIC METHODS FOR ADENOVIRUS PURIFICATION". SENESAC, Joseph WO2004037294A2 (May 6, 2004). "NEW SETTINGS FOR RECOMBINANT ADENOVIRAL-BASED VACCINES". HAVENGA, Menzo, Jans, Emco; HOLTERMAN, Lennart; KOSTENSE, Stefan; PAU, Maria, Grazia; SPRANGERS, Mieke, Caroline; VOGELS, Ronald WO2004055187A1 (Jul. 1, 2004). "RECOMBINANT VIRAL-BASED MALARIA VACCINES". PAU, Maria Grazia; HOLTERMAN, Lennart; KASPERS, Jorn; STEGMANN, Antonius, Johannes, Hendrikus WO2005002620A1 (Jan. 13, 2005). "QUIL A FRACTION WITH LOW TOXICITY AND USE THEREOF". MOREIN, Bror; LOVGREN BENGTSSON, Karin; EKSTROM, Jill; RANLUND, Katarina WO2005071093A2 (Aug. 4, 2005). "CHIMPANZEE ADENOVIRUS VACCINE CARRIERS". CIRILLO, Agostino; COLLOCA, Stefano; ERCOLE, Bruno, Bruni; MEOLA, Annalisa; NICOSIA, Alfredo; SPORENO, Elisabetta WO2005080556A2 (Sep. 1, 2005). "VIRUS PURIFICATION METHODS". WEGGEMAN, Miranda; VAN CORVEN, Emile Joannes Josephus Maria WO2006053871A2 (May 26, 2006). "MULTIVALENT VACCINES COMPRISING RECOMBINANT VIRAL VECTORS". HAVENGA, Menzo, Jans, Emco; VOGELS, Ronald; SADOFF, Jerald; HONE, David; SKEIKY, Yasir Abdul Wahid; RADOSEVIC, Katarina WO2006108707A1 (Oct. 19, 2006). "VIRUS PURIFICATION USING ULTRAFILTRATION". WEGGEMAN, Miranda WO2006120034A1 (Nov. 16, 2006). "VACCINE COMPOSITION". ERTL, Peter, Franz; TITE, John, Philip; VAN WELY, Catherine Ann WO2007073513A2 (Jun. 28, 2007). "METHOD FOR PROPAGATING ADENOVIRAL VECTORS ENCOD- ING INHIBITORY GENE PRODUCTS". GALL, Jason, G., D.; BROUGH, Douglas, E.; RICHTER, King, C.

WO2007100908A2 (Sep. 7, 2007). "CHIMERIC ADENOVIRAL VECTORS". TUCKER, Sean, N.

WO2007104792A2 (Sep. 20, 2007). "RECOMBINANT ADENOVIRUSES BASED ON SEROTYPE 26 AND 48, AND USE THEREOF". BAROUCH, Dan H.; HAVENGA, Menzo Jans Emko WO2007110409A1 (Oct. 4, 2007). "COMPOSITIONS COMPRISING A RECOMBINANT ADENOVIRUS AND AN ADJUVANT". HAVENGA, Menzo Jans Emko; RADOSEVIC, Katarina WO2009026183A1 (Feb. 26, 2009). "USE OF CHIMERIC HIV/SIV GAG PROTEINS TO OPTIMIZE VACCINE-INDUCED T CELL RESPONSES AGAINST HIV GAG". NABEL, Gary, J.; YANG, Zhi-Yong; SHI, Wei; BAROUCH, Dan, H.

WO2009117134A2 (Sep. 24, 2009). "AEROSOLIZED GENETIC VACCINES AND METHODS OF USE". ROEDERER, Mario; RAO, Srinivas; NABEL, Gary, J.; ANDREWS, Charla, Anne WO2010085984A1 (Aug. 5, 2010). "SIMIAN ADENOVIRUS NUCLEIC ACID- AND AMINO ACID-SEQUENCES, VECTORS CONTAINING SAME, AND USES THEREOF". COLLOCA, Stefano; NICOSIA, Alfredo; CORTESE, Riccardo; AMMENDOLA, Virginia; AMBROSIO, Maria WO2010086189A2 (Aug. 5, 2010). "SIMIAN ADENOVIRUS NUCLEIC ACID- AND AMINO ACID-SEQUENCES, VECTORS CONTAINING SAME, AND USES THEREOF". COLLOCA, Stefano; NICOSIA, Alfredo; CORTESE, Riccardo; AMMENDOLA, Virginia; AMBROSIO, Maria WO2010096561A1 (Aug. 26, 2010). "SYNTHETIC HIV/SIV GAG PROTEINS AND USES THEREOF". NABEL, Gary J.; YANG, Zhi-yong; SHI, Wei; BAROUCH, Dan H.

WO2011045378A1 (Apr. 21, 2011). "METHOD FOR THE PURIFICATION OF ADENOVIRUS PARTICLES". DE VOCHT, Marcel, Leo; VEENSTRA, Marloes WO2011045381A1 (Apr. 21, 2011). "PROCESS FOR ADENOVIRUS PURIFICATION FROM HIGH CELL DENSITY CULTURES". DE VOCHT, Marcel, Leo; VEENSTRA, Marloes WO2013139911A1 (Sep. 26, 2013). "VACCINE AGAINST RSV". RADOSEVIC, Katarina; CUSTERS, Jerôme H. H. V.; VELLINGA, Jort; WIDJOJOATMODJO, Myra N.

WO2013139916A1 (Sep. 26, 2013). "VACCINE AGAINST RSV". RADOSEVIC, Katarina; CUSTERS, Jerôme H. H. V.; VELLINGA, Jort; WIDJOJOATMODJO, Myra, N.

OTHER REFERENCES

Books

Ausubel et al., Current Protocols in Molecular Biology, Wiley Interscience Publishers, NY (1995)

Ausubel F. M., et al. (editors). Current Protocols in Molecular Biology; the series Methods in Enzymology, Academic Press, Inc. (1987)

Freshney, R. I., Culture of animal cells: A manual of basic technique, fourth edition, Wiley-Liss Inc., ISBN 0-471-34889-9 (2000)

Frokjaer S. and Hovgaard L. (editors), Pharmaceutical Formulation Development of Peptides and Proteins, Taylor & Francis (2000)

Gennaro, A. R. (editor), Remington's Pharmaceutical Sciences, 18th edition., Mack Publishing Company (1990)

Horowitz, M. S., Adenoviruses, Chapter 68, in Virology, (B. N. Fields et al. (editors), 3rd Ed., Raven Press, Ltd., New York (1996)

Kibbe A. (editor), Handbook of Pharmaceutical Excipients, 3rd edition, Pharmaceutical Press (2000)

Kruse and Paterson (editors), Tissue Culture, Academic Press. (1973)

MacPherson M. J., Hams B. D., Taylor G. R. (editors), PCR2: A Practical Approach (1995)

Sambrook et al., Molecular Cloning, a Laboratory Manual, 2nd Ed., Cold Spring Harbor Press, Cold Spring Harbor, N.Y. (1989)

Sambrook, Fritsch and Maniatis, Molecular Cloning: A Laboratory Manual, 2nd Ed., (1989)

Shenk, Thomas, Adenoviridae and their Replication, Chapter 67, in Virology, B. N. Fields et al. (editors)., 3rd Ed., Raven Press, Ltd., New York (1996)

Watson et al., Recombinant DNA, 2nd ed., Scientific American Books. (1992)

Journals

Abbink, P., Lemckert, A. A., Ewald, B. A., Lynch, D. M., Denholtz, M., Smits, S., . . . Barouch, D. H. (2007). Comparative seroprevalence and immunogenicity of six rare serotype recombinant adenovirus vaccine vectors from subgroups B and D. J Virol, 81(9), 4654-4663. doi: 10.1128/JVI.02696-06

Abrahamsen, K., Kong, H. L., Mastrangeli, A., Brough, D., Lizonova, A., Crystal, R. G., & Falck-Pedersen, E. (1997). Construction of an adenovirus type 7a E1A-vector. J Virol, 71(11), 8946-8951.

Amendola, M., Venneri, M. A., Biffi, A., Vigna, E., & Naldini, L. (2005). Coordinate dual-gene transgenesis by lentiviral vectors carrying synthetic bidirectional promoters. Nat Biotechnol, 23(1), 108-116.

Bangari, D. S., & Mittal, S. K. (2006). Development of nonhuman adenoviruses as vaccine vectors. Vaccine, 24(7), 849-862. doi: 10.1016/j.vaccine.2005.08.101

Belousova, N., Harris, R., Zinn, K., Rhodes-Selser, M. A., Kotov, A., Kotova, O., . . . Alvarez, R. D. (2006). Circumventing recombination events encountered with production of a clinical-grade adenoviral vector with a double-expression cassette. Mol Pharmacol, 70(5), 1488-1493.

Brough, D. E., Lizonova, A., Hsu, C., Kulesa, V. A., & Kovesdi, I. (1996). A gene transfer vector-cell line system for complete functional complementation of adenovirus early regions E1 and E4. J Virol, 70(9), 6497-6501.

Cohen, C. J., Xiang, Z. Q., Gao, G. P., Ertl, H. C., Wilson, J. M., & Bergelson, J. M. (2002). Chimpanzee adenovirus CV-68 adapted as a gene delivery vector interacts with the coxsackievirus and adenovirus receptor. J Gen Virol, 83(Pt 1), 151-155.

de Felipe, P., Luke, G. A., Brown, J. D., & Ryan, M. D. (2010). Inhibition of 2A-mediated 'cleavage' of certain artificial polyproteins bearing N-terminal signal sequences. Biotechnol J, 5(2), 213-223. doi: 10.1002/biot.200900134

Donnelly, M. L., Hughes, L. E., Luke, G., Mendoza, H., ten Dam, E., Gani, D., & Ryan, M. D. (2001). The 'cleavage' activities of foot-and-mouth disease virus 2A site-directed mutants and naturally occurring '2A-like' sequences. J Gen Virol, 82(Pt 5), 1027-1041.

Fallaux, F. J., Bout, A., van der Velde, I., van den Wollenberg, D. J., Hehir, K. M., Keegan, J., . . . Hoeben, R. C. (1998). New helper cells and matched early region 1-deleted adenovirus vectors prevent generation of replication-competent adenoviruses. *Hum Gene Ther,* 9(13), 1909-1917.

Farina, S. F., Gao, G. P., Xiang, Z. Q., Rux, J. J., Burnett, R. M., Alvira, M. R., . . . Wilson, J. M. (2001). Replication-defective vector based on a chimpanzee adenovirus. *J Virol,* 75(23), 11603-11613. doi: 10.1128/JVI.75.23.11603-11613.2001

Gao, G. P., Engdahl, R. K., & Wilson, J. M. (2000). A cell line for high-yield production of E1-deleted adenovirus vectors without the emergence of replication-competent virus. *Hum Gene Ther,* 11(1), 213-219. doi: 10.1089/10430340050016283

Geisbert, T. W., Bailey, M., Hensley, L., Asiedu, C., Geisbert, J., Stanley, D., . . . Sullivan, N. J. (2011). Recombinant adenovirus serotype 26 (Ad26) and Ad35 vaccine vectors bypass immunity to Ad5 and protect nonhuman primates against ebolavirus challenge. *J Virol,* 85(9), 4222-4233. doi: 10.1128/JVI.02407-10

Goerke, A. R., To, B. C., Lee, A. L., Sagar, S. L., & Konz, J. O. (2005). Development of a novel adenovirus purification process utilizing selective precipitation of cellular DNA. *Biotechnol Bioeng,* 91(1), 12-21. doi: 10.1002/bit.20406

Harro, C. D., Robertson, M. N., Lally, M. A., O'Neill, L. D., Edupuganti, S., Goepfert, P. A., . . . Mehrotra, D. V. (2009). Safety and immunogenicity of adenovirus-vectored near-consensus HIV type 1 clade B gag vaccines in healthy adults. *AIDS Res Hum Retroviruses,* 25(1), 103-114.

Havenga, M., Vogels, R., Zuijdgeest, D., Radosevic, K., Mueller, S., Sieuwerts, M., . . . Goudsmit, J. (2006). Novel replication-incompetent adenoviral B-group vectors: high vector stability and yield in PER.C6 cells. *J Gen Virol,* 87(Pt 8), 2135-2143.

Hoganson, D. K., Ma, J. C., Asato, L., Ong, M., Printz, M. A., Huyghe, B. G., . . . D'Andrea, M. J. (2002). Development of a Stable Adenoviral Vector Formulation. *BioProcessing J.,* 1(1), 43-48.

Holman, D. H., Wang, D., Raviprakash, K., Raja, N. U., Luo, M., Zhang, J., . . . Dong, J. Y. (2007). Two complex, adenovirus-based vaccines that together induce immune responses to all four dengue virus serotypes. *Clin Vaccine Immunol,* 14(2), 182-189.

Holterman, L., Vogels, R., van der Vlugt, R., Sieuwerts, M., Grimbergen, J., Kaspers, J., . . . Havenga, M. (2004). Novel replication-incompetent vector derived from adenovirus type 11 (Ad11) for vaccination and gene therapy: low seroprevalence and non-cross-reactivity with Ad5. *J Virol,* 78(23), 13207-13215. doi: 10.1128/JVI.78.23.13207-13215.2004

Hu, X., Meng, W., Dong, Z., Pan, W., Sun, C., & Chen, L. (2011). Comparative immunogenicity of recombinant adenovirus-vectored vaccines expressing different forms of hemagglutinin (HA) proteins from the H5 serotype of influenza A viruses in mice. *Virus Res,* 155(1), 156-162. doi: 10.1016/j.virusres.2010.09.014

Kobinger, G. P., Feldmann, H., Zhi, Y., Schumer, G., Gao, G., Feldmann, F., . . . Wilson, J. M. (2006). Chimpanzee adenovirus vaccine protects against Zaire Ebola virus. *Virology,* 346(2), 394-401. doi: 10.1016/j.virol.2005.10.042

Lasaro, M. O., & Ertl, H. C. (2009). New insights on adenovirus as vaccine vectors. *Mol Ther,* 17(8), 1333-1339. doi: 10.1038/mt.2009.130

Lemckert, A. A., Grimbergen, J., Smits, S., Hartkoorn, E., Holterman, L., Berkhout, B., . . . Havenga, M. J. (2006). Generation of a novel replication-incompetent adenoviral vector derived from human adenovirus type 49: manufacture on PER.C6 cells, tropism and immunogenicity. *J Gen Virol,* 87(Pt 10), 2891-2899. doi: 10.1099/vir.0.82079-0

Mullick, A., Xu, Y., Warren, R., Koutroumanis, M., Guilbault, C., Broussau, S., . . . Massie, B. (2006). The cumate gene-switch: a system for regulated expression in mammalian cells. *BMC Biotechnol,* 6, 43. doi: 10.1186/1472-6750-6-43

Na, M., & Fan, X. (2010). Design of Ad5F35 vectors for coordinated dual gene expression in candidate human hematopoietic stem cells. *Exp Hematol,* 38(6), 446-452. doi: 10.1016/j.exphem.2010.03.007

Nan, X., Peng, B., Hahn, T. W., Richardson, E., Lizonova, A., Kovesdi, I., & Robert-Guroff, M. (2003). Development of an Ad7 cosmid system and generation of an Ad7deltaE1deltaE3HIV(MN) env/rev recombinant virus. *Gene Ther,* 10(4), 326-336. doi: 10.1038/sj.gt.3301903

Ogun, S. A., Dumon-Seignovert, L., Marchand, J. B., Holder, A. A., & Hill, F. (2008). The oligomerization domain of C4-binding protein (C4 bp) acts as an adjuvant, and the fusion protein comprised of the 19-kilodalton merozoite surface protein 1 fused with the murine C4 bp domain protects mice against malaria. *Infect Immun,* 76(8), 3817-3823. doi: 10.1128/IAI.01369-07

Ophorst, O. J., Radosevic, K., Havenga, M. J., Pau, M. G., Holterman, L., Berkhout, B., . . . Tsuji, M. (2006). Immunogenicity and protection of a recombinant human adenovirus serotype 35-based malaria vaccine against *Plasmodium yoelii* in mice. *Infect Immun,* 74(1), 313-320.

Pham, L., Nakamura, T., Gabriela Rosales, A., Carlson, S. K., Bailey, K. R., Peng, K. W., & Russell, S. J. (2009). Concordant activity of transgene expression cassettes inserted into E1, E3 and E4 cloning sites in the adenovirus genome. *J Gene Med,* 11(3), 197-206.

Radosevic, K., Rodriguez, A., Lemckert, A. A., van der Meer, M., Gillissen, G., Warnar, C., . . . Goudsmit, J. (2010). The Th1 immune response to *Plasmodium falciparum* circumsporozoite protein is boosted by adenovirus vectors 35 and 26 with a homologous insert. *Clin Vaccine Immunol,* 17(11), 1687-1694. doi: 10.1128/CVI.00311-10

Schepp-Berglind, J., Luo, M., Wang, D., Wicker, J. A., Raja, N. U., Hoel, B. D., . . . Dong, J. Y. (2007). Complex adenovirus-mediated expression of West Nile virus C, PreM, E, and NS1 proteins induces both humoral and cellular immune responses. *Clin Vaccine Immunol,* 14(9), 1117-1126.

Small, J. C., Kurupati, R. K., Zhou, X., Bian, A., Chi, E., Li, Y., . . . Ertl, H. C. (2014). Construction and characterization of E1- and E3-deleted adenovirus vectors expressing two antigens from two separate expression cassettes. *Hum Gene Ther,* 25(4), 328-338. doi: 10.1089/hum.2013.216

Sullivan, N. J., Geisbert, T. W., Geisbert, J. B., Shedlock, D. J., Xu, L., Lamoreaux, L., . . . Nabel, G. J. (2006). Immune protection of nonhuman primates against Ebola virus with single low-dose adenovirus vectors encoding modified GPs. *PLoS Med,* 3(6), e177. doi: 10.1371/journal.pmed.0030177

Sullivan, N. J., Geisbert, T. W., Geisbert, J. B., Xu, L., Yang, Z. Y., Roederer, M., . . . Nabel, G. J. (2003). Accelerated vaccination for Ebola virus haemorrhagic fever in non-human primates. *Nature,* 424(6949), 681-684. doi: 10.1038/nature01876

Szymczak, A. L., Workman, C. J., Wang, Y., Vignali, K. M., Dilioglou, S., Vanin, E. F., & Vignali, D. A. (2004). Correction of multi-gene deficiency in vivo using a single 'self-cleaving' 2A peptide-based retroviral vector. *Nat Biotechnol,* 22(5), 589-594. doi: 10.1038/nbt957

Tatsis, N., Blejer, A., Lasaro, M. O., Hensley, S. E., Cun, A., Tesema, L., . . . Ertl, H. C. (2007). A CD46-binding chimpanzee adenovirus vector as a vaccine carrier. *Mol Ther,* 15(3), 608-617. doi: 10.1038/sj.mt.6300078

Vemula, S. V., & Mittal, S. K. (2010). Production of adenovirus vectors and their use as a delivery system for influenza vaccines. *Expert Opin Biol Ther,* 10(10), 1469-1487. doi: 10.1517/14712598.2010.519332

Vogels, R., Zuijdgeest, D., van Meerendonk, M., Companjen, A., Gillissen, G., Sijtsma, J., . . . Havenga, M. J. (2007). High-level expression from two independent expression cassettes in replication-incompetent adenovirus type 35 vector. *J Gen Virol,* 88(Pt 11), 2915-2924.

Vogels, R., Zuijdgeest, D., van Rijnsoever, R., Hartkoorn, E., Damen, I., de Bethune, M. P., . . . Havenga, M. (2003). Replication-deficient human adenovirus type 35 vectors for gene transfer and vaccination: efficient human cell infection and bypass of preexisting adenovirus immunity. *J Virol,* 77(15), 8263-8271.

Zhou, D., Cun, A., Li, Y., Xiang, Z., & Ertl, H. C. (2006). A chimpanzee-origin adenovirus vector expressing the rabies virus glycoprotein as an oral vaccine against inhalation infection with rabies virus. *Mol Ther,* 14(5), 662-672. doi: 10.1016/j.ymthe.2006.03.027

Zhou, D., Wu, T. L., Lasaro, M. O., Latimer, B. P., Parzych, E. M., Bian, A., . . . Ertl, H. C. (2010). A universal influenza A vaccine based on adenovirus expressing matrix-2 ectodomain and nucleoprotein protects mice from lethal challenge. *Mol Ther,* 18(12), 2182-2189. doi: 10.1038/mt.2010.202

The invention claimed is:

1. A recombinant adenovirus comprising a bidirectional mouse CMV (mCMV) promoter operably linked to a first transgene in one direction and to a second transgene in the opposite direction, wherein the recombinant adenovirus comprises an intron positioned 3' of the mouse CMV promoter and 5' of the first transgene and an intron positioned 3' of the mouse CMV promoter and 5' of the second transgene.

2. A recombinant adenovirus according to claim 1, wherein the adenovirus has a deletion in the E1 region.

3. A recombinant adenovirus according to claim 1, wherein the first and second transgene are different and at least one of them encodes an antigen.

4. A recombinant adenovirus according to claim 1, wherein the adenovirus is a human adenovirus serotype 35 or a human adenovirus serotype 26.

5. A method of producing a genetically stable recombinant adenovirus comprising a first and a second transgene that each are potently expressed when the adenovirus infects a target cell, the method comprising:
   a) preparing a construct comprising a bidirectional mouse CMV (mCMV) promoter operably linked to a first transgene in one direction and to a second transgene in the opposite direction, wherein the construct comprises an intron positioned 3' of the mouse CMV promoter and 5' of the first transgene and an intron positioned 3' of the mouse CMV promoter and 5' of the second transgene; and
   b) incorporating said construct into the genome of the recombinant adenovirus.

6. A method according to claim 5, wherein the recombinant adenovirus has a deletion in the E1 region of its genome.

7. A method according to claim 5, wherein the first and second transgene are different and at least one of them encodes an antigen.

8. A method according to claim 5, wherein the recombinant adenovirus is a human adenovirus serotype 35 or a human adenovirus serotype 26.

9. A method for expressing at least two transgenes in a cell, the method comprising providing a cell with a recombinant adenoviral vector according to claim 1.

10. A method for inducing an immune response against at least two antigens, the method comprising administering to a subject a recombinant adenoviral vector according to claim 1.

11. A pharmaceutical composition comprising a recombinant adenovirus according to claim 1 and a pharmaceutically acceptable carrier or excipient.

* * * * *

SEQUENCE LISTING

<160> NUMBER OF SEQ ID NOS: 4

<210> SEQ ID NO 1
<211> LENGTH: 1958
<212> TYPE: DNA
<213> ORGANISM: Mouse cytomegalovirus

<400> SEQUENCE: 1
cacggccaag gtcagcaccg cagcttttat cctgaagggc cgtgggggac ctggaggaga 60
agaagggcct ggctgagtgg gtgccttcag tatgcagaag ccccgtgctc cccgaactca 120
gttgcagcca ggtgaggaga agggcacaga gcgggagaag acctcaggta ccagaggccc 180
ggcctggggc aaggcctgaa ccttgagctg gggagccaga gtgaccgggg caggcagcag 240
gacgcacctc cttctcgcag tctctaagca gccagctctt gcagggccta tttatgtgtt 300
aacgtaggta gggtcgtatc gagccgcggt ccgtcctgct ctgggctcga atggcatggg 360
ggacagcaat tatatggtta actccgcccg ttttatgact agaaccaata gtttttaatg 420
ccaaatgcac tgaaatcccc taatttgcaa agccaaacgc cccctatgtg agtaatacgg 480
ggacttttta cccaatttcc cacgcggaaa gccccctaat acactcatat ggcatatgaa 540
tcagcacggt catgcactct aatggcggcc catagggact ttccacatag ggggcgttca 600
ccatttccca gcataggggt ggtgactcaa tggcctttac ccaagtacat tgggtcaatg 660
ggaggtaagc caatgggttt ttcccattac tggcaagcac actgagtcaa atgggacttt 720
ccactgggtt ttgcccaagt acattgggtc aatgggaggt gagccaatgg gaaaaaccca 780
ttgctgccaa gtacactgac tcaataggga ctttccaatg ggtttttcca ttgttggcaa 840
gcatataagg tcaatgtggg tgagtcaata gggactttcc attgtattct gcccagtaca 900
taaggtcaat agggggtgaa tcaacaggaa agtcccattg gagccaagta cactgcgtca 960
atagggactt tccattgggt tttgcccagt acataaggtc aataggggat gagtcaatgg 1020
gaaaaaccca ttggagccaa gtacactgac tcaataggga ctttccattg ggttttgccc 1080
agtacataag gtcaataggg ggtgagtcaa caggaaagtt ccattggagc caagtacatt 1140
gagtcaatag ggactttcca atgggttttg cccagtacat aaggtcaatg ggaggtaagc 1200
caatgggttt ttcccattac tggcacgtat actgagtcat tagggacttt ccaatgggtt 1260
ttgcccagta cataaggtca ataggggtga atcaacagga aagtcccatt ggagccaagt 1320

```
acactgagtc aataagggact ttccattggg ttttgcccag tacaaaaggt caataggggg   1380
tgagtcaatg ggttttttccc attattggca cgtacataag gtcaataggg gtgagtcatt   1440
gggttttttcc agccaattta atttaaacgc catgtacttt cccaccattg acgtcaatgg   1500
gctattgaaa ctaatgcaac gtgacccttta acggtactt tcccatagct gattaatggg    1560
aaagtaccgt tctcgagcca atacacgtca atgggaagtg aaagggcagc caaaacgtaa   1620
caccgccccg ttttcccct ggaaattcca tattggcacg cattctattg ctgagctgc     1680
gttctacgtg gtataagag cgcgaccag cgtcggtacc gtcgcagtct tcggtctgac     1740
caccgtagaa cgcagagctc ctcgctgcag ctgcagaagt tggtcgtgag gcactgggca   1800
ggtaagtatc aaggttacaa gacaggttta aggagaccaa tagaaactgg gcttgtcgag   1860
acagagaaga ctcttgcgtt tctgataggc acctattggt cttactgaca tccactttgc   1920
ctttctctcc acaggtgtcc actcccagtt caattaca                           1958

<210> SEQ ID NO 2
<211> LENGTH: 1478
<212> TYPE: DNA
<213> ORGANISM: Mouse cytomegalovirus

<400> SEQUENCE: 2
gttaacgtag gtagggtcgt atcgagccgc ggtccgtcct gctctgggct cgaatggcat     60
gggggacagc aattatatgg ttaactccgc ccgttttatg actagaacca atagttttta    120
atgccaaatg cactgaaatc ccctaatttg caaagccaaa cgcccctat gtgagtaata    180
cggggacttt ttacccaatt tcccacgcgg aaagccccct aatacactca tatggcatat    240
gaatcagcac ggtcatgcac tctaatggcg gcccataggg actttccaca taggggggcgt  300
tcaccatttc ccagcatagg ggtggtgact caatggcctt tacccaagta cattgggtca    360
atgggaggta agccaatggg ttttttcccat tactggcaag cacactgagt caaatgggac    420
tttccactgg gttttgccca agtacattgg gtcaatggga ggtgagccaa tgggaaaaac    480
ccattgctgc caagtacact gactcaatag ggactttcca atgggttttt ccattgttgg    540
caagcatata aggtcaatgt gggtgagtca atagggactt tccattgtat tctgcccagt    600
acataaggtc aatagggggt gaatcaacag gaaagtccca ttggagccaa gtacactgcg   660
tcaataggga cttccattg ggttttgccc agtacataag gtcaataggg gatgagtcaa    720
tgggaaaaac ccattggagc caagtacact gactcaatag ggactttcca ttgggttttg   780
cccagtacat aaggtcaata gggggtgagt caacaggaaa gttccattgg agccaagtac   840
attgagtcaa tagggactt ccaatgggtt tttgcccagta cataaggtca atgggaggta    900
agccaatggg ttttttcccat tactggcacg tatactgagt cattagggac tttccaatgg   960
gttttgccca gtacataagg tcaataggggg tgaatcaaca ggaaagtccc attggagcca   1020
agtacactga gtcaataggg actttccatt gggttttgcc cagtacaaaa ggtcaatagg   1080
gggtgagtca atgggttttt cccattattg gcacgtacat aaggtcaata ggggtgagtc   1140
attgggtttt tccagccaat taattttaaa cgccatgtac tttcccacca ttgacgtcaa    1200
tgggctattg aaaactaatg caacgtgacct ttaaacggta cttccccata gctgattaat   1260
gggaaagtac cgttctcgag ccaatacacg tcaatgggaa gtgaaaggggc agccaaaacg   1320
taacaccgcc ccggttttcc cctggaaatt ccatatttggc acgcattcta ttggctgagc   1380
tgcgttctac gtgggtataa gaggcgcgac cagcgtcggt accgtcgcag tcttcggtct   1440
gaccaccgta gaacgcagag ctcctcgctg cagctgca                           1478
```

```
<210> SEQ ID NO 3
<211> LENGTH: 183
<212> TYPE: DNA
<213> ORGANISM: Artificial Sequence
<220> FEATURE:
<223> OTHER INFORMATION: Chimeric intron

<400> SEQUENCE: 3
gaagttggtc gtgaggcact gggcaggtaa gtatcaaggt tacaagacag gtttaaggag      60
accaatagaa actgggcttg tcgagacaga gaagactctt gcgtttctga taggcaccta     120
ttggtcttac tgacatccac tttgcctttc tctccacagg tgtccactcc cagttcaatt     180
aca                                                                    183

<210> SEQ ID NO 4
<211> LENGTH: 297
<212> TYPE: DNA
<213> ORGANISM: Homo sapiens

<400> SEQUENCE: 4
acataaatag gccctgcaag agctggctgc ttagagactg cgagaaggag gtgcgtcctg      60
ctgcctgccc cggtcactct ggctccccag ctcaaggttc aggccttgcc ccaggccggg     120
cctctggtac ctgaggtctt ctcccgctct gtgcccttct cctcacctgg ctgcaactga     180
gttcggggag cacggggctt ctgcatactg aaggcaccca ctcagccagg cccttcttct     240
cctccaggtc ccccacggcc cttcaggata aaagctgcgg tgctgacctt ggccgtg        297
```